(12) United States Patent
Downing

(10) Patent No.: US 6,840,246 B2
(45) Date of Patent: Jan. 11, 2005

(54) APPARATUSES AND METHODS FOR PERFORMING MINIMALLY INVASIVE DIAGNOSTIC AND SURGICAL PROCEDURES INSIDE OF A BEATING HEART

(75) Inventor: Stephen W. Downing, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/881,045

(22) Filed: Jun. 15, 2001

(65) Prior Publication Data

US 2002/0161378 A1 Oct. 31, 2002

Related U.S. Application Data

(60) Provisional application No. 60/212,075, filed on Jun. 20, 2000.

(51) Int. Cl.[7] .............................................. A61B 19/00
(52) U.S. Cl. ..................... 128/898; 606/219; 227/175.1
(58) Field of Search ................................ 606/108, 191, 606/219, 228; 604/167.01–167.04; 623/2.36, 2.38, 2.39; 227/175.1; 128/898

(56) References Cited

U.S. PATENT DOCUMENTS

| | | | | |
|---|---|---|---|---|
| 4,000,739 A | * | 1/1977 | Stevens ....................... | 604/537 |
| 5,332,402 A | * | 7/1994 | Teitelbaum .................. | 623/2.42 |
| 5,591,195 A | * | 1/1997 | Taheri et al. ................ | 623/1.11 |
| 5,797,933 A | * | 8/1998 | Snow et al. .................. | 606/151 |
| 5,797,960 A | * | 8/1998 | Stevens et al. .............. | 606/213 |
| 5,957,949 A | * | 9/1999 | Leonhardt et al. .......... | 623/1.24 |
| 5,972,030 A | * | 10/1999 | Garrison et al. ............ | 623/2.11 |
| 6,059,750 A | * | 5/2000 | Fogarty et al. ......... | 604/103.07 |
| 6,231,587 B1 | * | 5/2001 | Makower ..................... | 606/198 |
| 6,287,322 B1 | * | 9/2001 | Zhu et al. .................... | 606/213 |

OTHER PUBLICATIONS

Cohn, L.H., et al., "Mechanical and Bioprosthetic Mitral Valve Replacement", Cardiac Surgery in the Adult, McGraw–Hill, Health Professions Division, 34, 1025–1050 (1997).

Cosgrove III, D.M., et al., "Minimally Invasive Valve Operations", Ann. Thorac. Surg., 65, 1535–1539 (1998).

Navia, J.L., et al., "Minimally Invasive Mitral Valve Operations", Ann. Thorac. Surg., 62, 1542–1544 (1996).

Aklog, L. et al., "Techniques and Results of Direct–Access Minimally Invasive Mitral Valve Surgery: A Paradigm for the Future", Journal of Thoracic and Cardiovascular Surgery, 705–715 (1998).

Cohn, L.H., et al., "Minimally Invasive Cardiac Valve Surgery Improves Patient Satisfaction While Reducing Costs of Cardiac Valve Replacement and Repair", Annals of Surgery, 226, 4, 421–428 (1997).

Loulmet, D.F., et al., "Less Invasive Techniques for Mitral Valve Surgery", Journal of Thoracic and Cardiovascular Surgery, 115, 772–779 (1998).

Mohr, F.W., et al., "Minimally Invasive Port–Access Mitral Valve Surgery", Journal of Thoracic and Cardiovascular Surgery, 115, 567–576 (1998).

(List continued on next page.)

Primary Examiner—Julian W. Woo
Assistant Examiner—Victor Nguyen
(74) Attorney, Agent, or Firm—Carol M. LaSalle; Bozicevic, Field & Francis LLP

(57) ABSTRACT

Diagnostic and surgical procedures may be performed on a beating heart using an assembly which includes a port and a fluid transport device. The port has a housing for insertion through a wall of the heart chamber and may include one valve disposed in the housing and an inlet connected to the housing. Methods for repair and diagnosis of the heart are also described. A specific method for repairing a mitral valve uses staples which may be banded together with a strip of material.

4 Claims, 21 Drawing Sheets

OTHER PUBLICATIONS

Chitwood, Jr., W.R., et al., "Video–Assisted Minimally Invasive Mitral Valve Surgery: The "Micro–Mitral" Operation", Journal of Thoracic and Cardiovascular Surgery, 113, 2, 413–414 (1997).

Gundry, S.R., et al., "Facile Minimally Invasive Cardiac Surgery via Ministernotomy", Ann. Thorac. Surg., 65, 1100–1104 (1998).

Baldwin, J.C., "Surgery for Acquired Heart Disease, Editorial (Con) Re Minimally Invasive Port–Access Mitral Valve Surgery", Journal of Thoracic and Cardiovascular Surgery, 115, 563–564 (1998).

Buckberg, G.D., et al., "Integrated Myocardial Management: Background and Initial Application", Journal Card. Surg., 10, 68–89 (1995).

Kirklin, J.W., "Myocardial Management During Cardiac Surgery With Cardiopulmonary Bypass", Cardiac Surgery, 3, 129–165 (1993).

Gorman, R.C., et al., "Cardiopulmonary Bypass, Myocardial Management, and Support Techniques, Surface–Bound Heparin Fails to Reduce Thrombin Formation During Clinical Cardiopulmonary Bypass", Journal of Thoracic and Cardiovascular Surgery, 111, 1, 1–12 (1996).

Edmunds, Jr., L.H., "Blood–Surface Interactions During Cardiopulmonary Bypass", Journal Card. Surg., 8, 404–410 (1993).

Chung, J.H., et al., "Pericardial Blood Activates the Extrinsic Coagulation Pathway During Clinical Cardiopulmonary Bypass", Circulation, 93, 11, 2014–2018 (1996).

Edmunds, Jr., L.H., "Why Cardiopulmonary Bypass Makes Patients Sick: Strategies to Control the Blood–Synthetic Surface Interface", Advances in Cardiac Surgery, 6, 131–167 (1995).

Edmunds, Jr., L.H., "Inflammatory Response to Cardiopulmonary Bypass", Ann. Thorac. Surg., 66, S12–S16 (1998).

Downing, S.W., et al., "Release of Vasoactive Substances During Cardiopulmonary Bypass", Ann. Thorac. Surg., 54, 1236–1243 (1992).

Westaby, S., et al., "Less Invasive Coronary Surgery: Consensus From the Oxford Meeting", Ann. Thorac. Surg., 62, 924–931 (1996).

Siminelakis, S., et al., "A Study of the Effects of Extracorporeal Circulation on the Immunologic System of Humans", Journal of Cardiothoracic and Vascular Anesthesia, 10, 7, 893–898 (1996).

Gill, R., et al., "Neuropsychologic Dysfunction After Cardiac Surgery: What Is the Problem?", Journal of Cardiothoracic and Vascular Anesthesia, 10, 1, 91–98 (1996).

Taylor, K., "Brain Damage During Cardiopulmonary Bypass", Ann. Thorac. Surg., 65, 20–26 (1998).

Taylor, K.M., "Central Nervous System Effects of Cardiopulmonary Bypass", Ann. Thorac. Surg., 66, 20–24 (1998).

Roach, G.W., et al., "Adverse Cerebral Outcomes After Coronary Bypass Surgery", New England Journal of Medicine, 335, 25, 1857–1863 (1996).

Jansen, E.W., et al., "Less Invasive Off–Pump CABG Using a Suction Device for Immobilization: the 'Octopus' Method", European Journal of Cardio–thoracic Surgery, 12, 3, 406–412 (1997).

Takuma, S., et al., "Evaluation of Mitral Valve Disease Using Transesophageal Echocardiography", Seminars in Thoracic and Cardiovascular Surgery, 10, 4, 247–254 (1998).

Daniel, W.G., et al., "Transesophageal Echocardiography", New England Journal of Medicine, 332, 1268–1279 (1995).

Foster, G.P., et al., "Accurate Localization of Mitral Regurgitant Defects Using Multiplane Transesophageal Echocardiography", Ann. Thorac. Surg., 65, 1025–1031 (1998).

Takuma, S., et al., "Real–Time, 3–Dimensional Echocardiography Acquires All Standard 2–Dimensional Images From 2 Volume Sets: A Clinical Demonstration in 45 Patients", Journal of the American Society of Echocardiography, 12, 1, 1–6 (1999).

Umaña, J.P., et al., "'Bow–Tie' Mitral Valve Repair: An Adjuvant Technique for Ischemic Mitral Regurgitation", Ann. Thorac. Surg., 66, 1640–1646 (1998).

Morales, D.L.S., et al., "Development of an Off Bypass Mitral Valve Repair", Heart Surgery Forum, 2 (2), 115–120 (1999).

St. Jude Medical Corporation, 1998: Personal Communication.

* cited by examiner

APPARATUSES AND METHODS FOR PERFORMING MINIMALLY INVASIVE DIAGNOSTIC AND SURGICAL PROCEDURES INSIDE OF A BEATING HEART

This application claims the benefit of U.S. Provisional Application No. 60/212,075, filed Jun. 20, 2000, incorporated by reference herein in its entirety.

FIELD OF THE INVENTION

The present invention relates generally to an apparatuses and methods for performing minimally invasive diagnostic and surgical procedures inside of a beating heart. More particularly, the present invention relates to an apparatuses and methods for accessing the heart chamber and performing minimally invasive diagnostic and surgical procedures, including diagnosing and repairing pathology of the heart valves (aortic, mitral, pulmonary and tricuspid) and the cardiac chambers (atrial and ventricular septums), inside of a heart while the heart is still beating.

BACKGROUND OF THE INVENTION

Diagnostic and reparative surgical procedures have been performed on the heart since at least the 1920s. The first attempts at repairing heart valves began in 1923 with Cutler and Levine performing blind dilations of the mitral valve with cutting instruments. These dilations were blind in that the patient's blood blocked the surgeon's sight to the valve. Thereafter, Sutar reported a successful dilation of a stenotic, or narrowed, mitral valve by inserting his finger through the atrium across the valve. The technique of digital dilation was improved and championed by Harken in 1948 and Bailey in 1949. Later, more effective instruments were developed, such the Tubbs dilator, which can be placed through a purse-string suture in either the atrium or the ventricle, passed across the valve, and dilated. These various techniques were somewhat effective to repair heart valves, but operating "blind" made precision impossible, and dilation often tore the valve, leading to valvular insufficiency. In addition, embolic brain and other organ injuries occurred due to air entering the heart chambers and to loosening calcific debris.

The field of cardiac valve surgery did not develop significantly further until introduction, by Gibbon (1953) and by Lillehei and Kirklin (1955), of the heart-lung machine and cardiopulmonary bypass technique (CPB). With the body fully supported by CPB, the heart could be stopped with a protective cold blood potassium solution (cardioplegia) and opened, and more precise valve repairs and replacements could be performed under direct vision. At present, approximately 130,000 to 150,000 mitral valve procedures are performed annually. (1). All require full CPB, cardiac arrest, and a thoracic incision.

The repair of septal defects, i.e., holes in the walls of the cardiac chambers, followed a similar course. Several surgeons attempted to repair atrial septal defects in a beating heart by placing sutures blindly through the chamber walls or by working through atrial wells. These "wells" were created by "dams" sewn into the atrium. Once the well was constructed, the heart chamber was opened. The blood would rise a few centimeters up the walls of the well, due the pressure in the heart chamber. The relatively low pressure in the atrium, ranging from 2–20 mmHg, kept the blood from rising more than a few centimeters. The repair then was performed through the well.

Like the valve repairs, this procedure was a blind one, due to the surgeon's inability to see through blood that collected in the heart chamber. In addition, blood loss was unpredictable. Further, it was easy to entrain air into the cardiac chamber during this procedure, which could cause heart failure, strokes, and death. Several creative methods were devised to temporarily stop blood flow or briefly turn off the circulation or to support the circulation using another person's circulatory system, but these methods were cumbersome and dangerous, and only the simplest repairs could be performed. Safe and effective chamber wall repairs did not truly begin until introduction of the heart lung machine. The heart-lung machine supported circulation so that the surgeon could repair the septal defect under direct vision.

With the advent of the heart-lung machine, CPB became the preferred method of cardiac surgery. The standard CPB procedure requires opening the chest, placing the patient on CPB, and stopping the heart with cardioplegia. The heart itself is then opened and repaired. Heart valves replaced or repaired by various techniques, and defects in the atrial and ventricular septums can be sutured closed directly, or a patch can be sewn into place over the septum.

Despite advances, many open-heart surgical procedures still have a 5–9% mortality rate and a 20% morbidity rate. (2). In order to reduce morbidity, several "less invasive" approaches have been developed. Specialized clamps and cannulas allow the patient to be placed on CPB though smaller chest incisions or via a femoral approach. (3–8). Alterations in technique, new instruments, and the use of video have been utilized to further reduce incision size. (9). These advances improve patient satisfaction and may improve return-to-work rates. (6, 10).

The advances have not reduced the major complication rates, however, and they are associated with an increased risk of aortic dissection and stroke. Further, they increase the cost per case by approximately $5000. (8, 11). The major complication rate has not been reduced because the procedures have not eliminated the need for cardioplegia and CPB, which together account for the majority of the complications.

When the heart is stopped for surgery, it is cut off from its blood supply. Cardioplegia, administered by one of several techniques, can minimize heart injury. (12). However, cardiac function is always depressed after cardioplegic arrest, and the longer the duration of arrest, the greater the injury. (13). In addition to the risks associated with cardioplegia, CPB, in its own right, can be damaging in multiple ways. CPB causes bleeding by disrupting hemostasis (blood clotting). CPB consumes platelets, activates fibrinogen, generates fibrin split products, activates the contact activation system, and dilutes formed and plasma clotting elements. (14–17). CPB also elicits a substantial whole body inflammatory response and generates large numbers of vasoactive substances. (17–19). This leads to pulmonary dysfunction, third space loss, and neurohumoral imbalances. (17, 20). Additionally, CPB has negative effects on the immune system. (21). Furthermore, macroemboli produced during cannulation and aortic cross-clamping, as well as gaseous and particulate microemboli generated during the period of CPB, have been implicated in neurologic dysfunction seen frequently after open heart surgery. (22–24). A recent article in the *New England Journal of Medicine* reported that up to 6.1% of patients have adverse cerebral outcomes after cardiac surgery, with the majority of events attributable to CPB. (25).

Several approaches have been developed to perform coronary artery bypass grafting on the beating heart using stabilization technologies. (26). These approaches eliminate the need for cardioplegia and CPB, reducing morbidity and per case cost. (20). Surgery of the interior of the heart is not possible with these methods, however, because the methods do not allow the cardiac chambers to be opened. To do surgery on the heart without CPB, the heart must continue to beat. Opening the cardiac chambers of a beating heart would lead to massive blood loss and air being drawn into the circulation in large amounts. Additionally, in order to directly visualize the area of surgical interest, the cardiac chamber must be free of blood. This cannot occur while the heart is beating.

Cardiac surgery is undergoing a rapid evolution to less and less invasive procedures. Valve repairs and replacements can now be performed through significantly smaller incisions. Dr. Mehmet Oz at Columbia University has reported of a clip device that can be inserted through the apex of the left ventricle of the heart and clipped onto the leaflets of the mitral valve. (32). The clip effectively sews the anterior leaflet to the posterior leaflet. This clip technique mimics one type of mitral valve repair, called a "bow-tie" or Alfiori repair, and, as best understood, currently requires CPB. The clip technique has some potential drawbacks, however, including possible device embolization. In addition, entering the heart through the apex of the left ventricle increases the risk of blood loss due to the high intracavitary pressures of the ventricle and does not allow for any other work to be performed on the mitral valve.

SUMMARY OF THE INVENTION

The present invention is drawn to apparatuses and methods for performing minimally invasive diagnostic and surgical procedures inside of a beating heart that alleviate the need for cardiopulmonary bypass (CPB), minimizes the risk of air introduction into the heart during surgery and emboli, and maintains sufficient intracardial pressure during the diagnostic and surgical procedures. In addition, the apparatuses and methods are compatible with several types of diagnostic and surgical techniques, including mitral valve repair, repair of atrial or ventricular septal defects, endovascular aortic surgery, and electrophysiologic studies.

A cardiac port for insertion through a chamber wall of a heart chamber to perform a medical procedure inside of a beating heart in accordance with the invention includes a housing, at least one valve, and an inlet. The housing has a first end, a second end, and a lumen therethrough. The valve is disposed in the housing to open and close the lumen. The inlet is connected to the housing. The inlet has an inlet passage in fluid communication with the lumen of the housing. The inlet is adapted to transmit a fluid between an exterior of the port and the lumen of the housing.

In another arrangement of the invention, a cardiac port for insertion through a chamber wall of a heart chamber to perform a medical procedure inside of a beating heart includes a housing, at least one valve, and first and second retainer members. The housing has a first end, a second end, and a lumen therethrough. The valve is disposed in the housing to open and close the lumen. The first and second retainer members are located on the housing. The first retainer member is spaced from the second retainer member a predetermined distance to anchor the chamber wall between the first and second retainer members. The first and second retainer members can comprise first and second flanges disposed on an exterior surface of the housing.

In another aspect of the invention, an assembly for use in performing a medical procedure inside of a beating heart of a patient includes a port and a fluid transport device. The port in turn includes a housing having a first end, a second end, and a lumen therethrough; at least one valve disposed in the housing to open and close the lumen; and an inlet connected to the housing. The housing is configured for insertion through a chamber wall of a heart chamber so that the first end is exterior of the chamber wall and the second end is interior of the chamber wall. The inlet has an inlet passage in fluid communication with the lumen of the housing. The fluid transport device has one end that attaches to the inlet of the port, another end that attaches to a fluid source, and a fluid channel therebetween to pass a fluid from the fluid source to the inlet. The fluid passes from the inlet through the inlet passage and through the lumen into the heart chamber to maintain an intra-chamber pressure at a desired level.

A method of accessing an interior of a heart chamber of a heart in accordance with the invention comprises the steps of maintaining beating of the heart, and inserting a port in a chamber wall of the heart chamber, the port having a lumen therethrough for accessing the interior of the heart chamber from exterior of the heart chamber. The inserting step can comprise securing the port in an atrial wall to access an interior of the heart.

In still another aspect of the invention, a method of preparing a beating heart for a diagnostic or medical procedure comprises the steps of inserting a port in a chamber wall of the beating heart, the port having a lumen to access to the heart chamber; and pressurizing the heart chamber with blood from a patient's artery. The method can include positioning a cannula through the chamber wall, and the pressurizing step can be accomplished by shunting arterial blood from the patient's artery into the heart chamber via the cannula. In another arrangement, the pressurizing step can be accomplished by shunting arterial blood from the patient's artery into the heart chamber via the port.

An apparatus for cutting a suture in accordance with the invention comprises an elongated body and a cutting implement. The elongated body, or sheath, has a lumen, a wall member extending into the lumen, and a knot-receiving chamber defined by a first area on a first side of the wall member. The wall member defines a channel therethrough, where the channel is dimensioned to permit passage of a suture and to prevent passage of a knot. The cutting implement is movably disposed in the lumen in a second area on a second side of the wall member opposite the first side. The cutting implement is movable between a first position and second position to cut the suture. The suture cutting apparatus also can include an actuator to move the cutting implement between the first position and the second position.

A method for repairing a damaged heart valve of a beating heart in accordance with the invention comprises the steps of inserting a valved port in a chamber wall of the beating heart to access an interior of a heart chamber; inserting a stapling device through the valved port; and positioning staples from the stapling device into at least a portion of the mitral valve annulus of the damaged heart valve to reduce a length of the portion of the mitral valve annulus. The method also can comprise the step of connecting the staples together with a strip of material. The positioning step can be accomplished by positioning the staples into the posterior mitral annulus.

The apparatuses and methods of the present invention provide several advantages over known cardiac surgical instrumentation and procedures. For example, the apparatuses and methods of the present invention alleviate the need for CPB or cardioplegic arrest by combining a cardiac port with advances in cardiac imaging and endoscopic suture placement devices and stapling devices and simplified valve and septal defect repair techniques. The cardiac port of the present invention is configured to be inserted through a chamber wall of a beating heart and to enable passage of medical instruments into a heart chamber, while minimizing injection of air into the heart chambers and consequent emboli. The method of the present invention provides access to a heart chamber via the cardiac port so that the surgical instruments can be inserted through the heart chamber to gain access to the operative site.

The advances in cardiac imaging include multiplane trans-esophageal echocardiography (TEE). For example, in mitral valve repair, TEE images the mitral valve well enough to allow surgical manipulation of the valve via instruments, such as endoscopic suture placement devices, inserted into the heart chamber through the cardiac port. In one surgical technique, the endoscopic suture placement device can grasp the edge of a moving mitral valve leaflet and pass a suture through the valve leaflet. The endoscopic suture placement device, in essence, sews the valve. This surgical technique involves suturing the free edges of the anterior and posterior mitral valves together to replicate an Alfiori ("bow tie") mitral valve repair. The method of the present invention also enables investigation of the hemodynamic consequences of temporary acute mitral valve incompetence that will occur with valve manipulation.

In addition, the apparatuses and methods of the present invention enable the surgeon to enter the heart through the atrium. The atrial approach allows the surgeon to place additional sutures and annuloplasty devices, including staples, sutures, and rings, in the appropriate locations in the heart. Further, an atrial approach, as compared to a ventricular approach, minimizes blood loss and maximizes the types of surgical techniques that can be performed.

These features and advantages, as well as other features and advantages, of the present invention will be set forth in the description that follows.

BRIEF DESCRIPTION OF THE DRAWINGS

These and other features, aspects, and advantages of the present invention will become apparent from the following detailed description, appended claims, and the accompanying exemplary embodiment shown in the drawings, which are briefly described below.

DETAILED DESCRIPTION OF A PREFERRED EMBODIMENT

The present invention provides apparatuses and methods for performing minimally invasive diagnostic and surgical procedures inside of a beating heart, thereby obviating the need for administration of cardioplegia and cardiopulmonary bypass (CPB). Procedures contemplated by the present invention can include mitral and tricuspid valve repair, aortic and pulmonary valve repair, and repair of intracardiac defects, such as atrial and ventricular septal defects. Repair of the mitral valve in turn can include correcting mitral regurgitation (i.e., annular dilation and heart failure, myxomatous degeneration, and chordal rupture) and mitral stenosis. Other procedures include adjuncts to endovascular surgery and access for electrophysiologic studies. One of ordinary skill in the art will recognize other applications for the present apparatuses and methods.

In this connection, the present invention provides a valved cardiac port that can be temporarily inserted in a chamber wall of a heart chamber of a beating heart to provide access to the interior of the heart chamber from exterior of the heart chamber. In a preferred embodiment, the cardiac port is positioned through the wall of the left atrium. The atrium, as opposed to the ventricle, is the preferred port of entry into the heart due to its anatomic position (i.e., enables access to the valve annulus, which is important in several valve repair techniques), low pressure, large surface area, lack of epicardial vessels to injure with port insertion, and relatively thin and flexible wall that facilitates instrument insertion and manipulation.

In another aspect of the invention, the operative heart chamber can be kept pressurized with the patient's own blood. Pressurization is important to minimize the risk of air and/or particulates being introduced into the heart chamber and to minimize emboli. In a first technique, a catheter can be run between the patient's femoral or radial artery and the cardiac port to shunt the patient's blood into the cardiac chamber via the cardiac port. In a second technique, a catheter can be run between the femoral or radial artery to a cannula or a second port positioned at another location in the chamber wall, and the patient's blood can be introduced into the cardiac chamber via the cannula or the second port.

Figure 1:
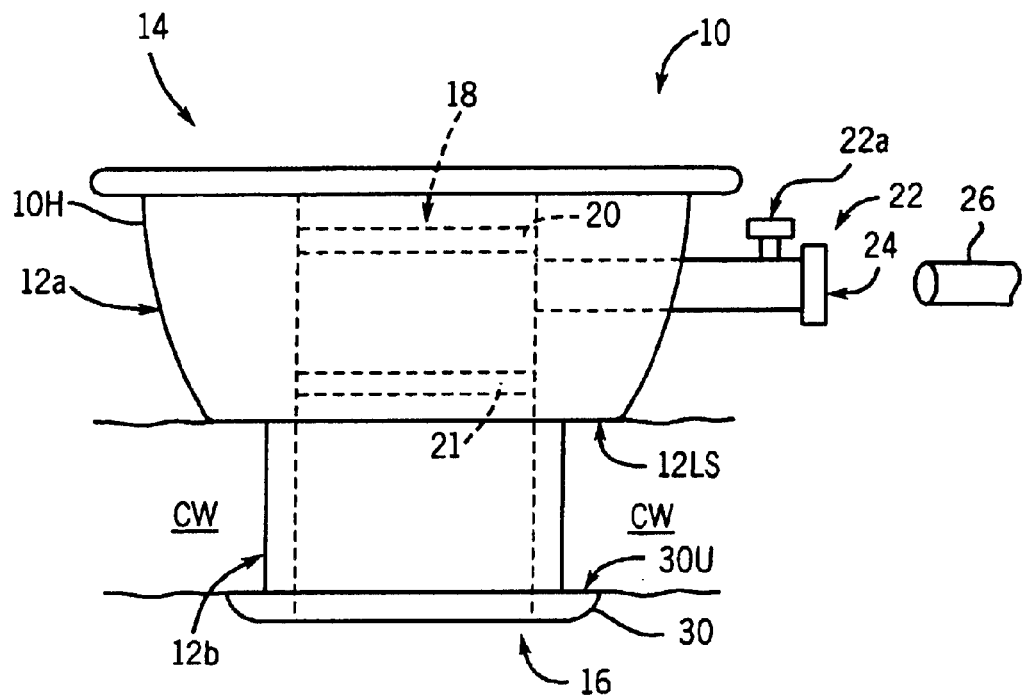
FIG. 1 is a side elevation view of a cardiac port in accordance with the invention.
Figure 1A:
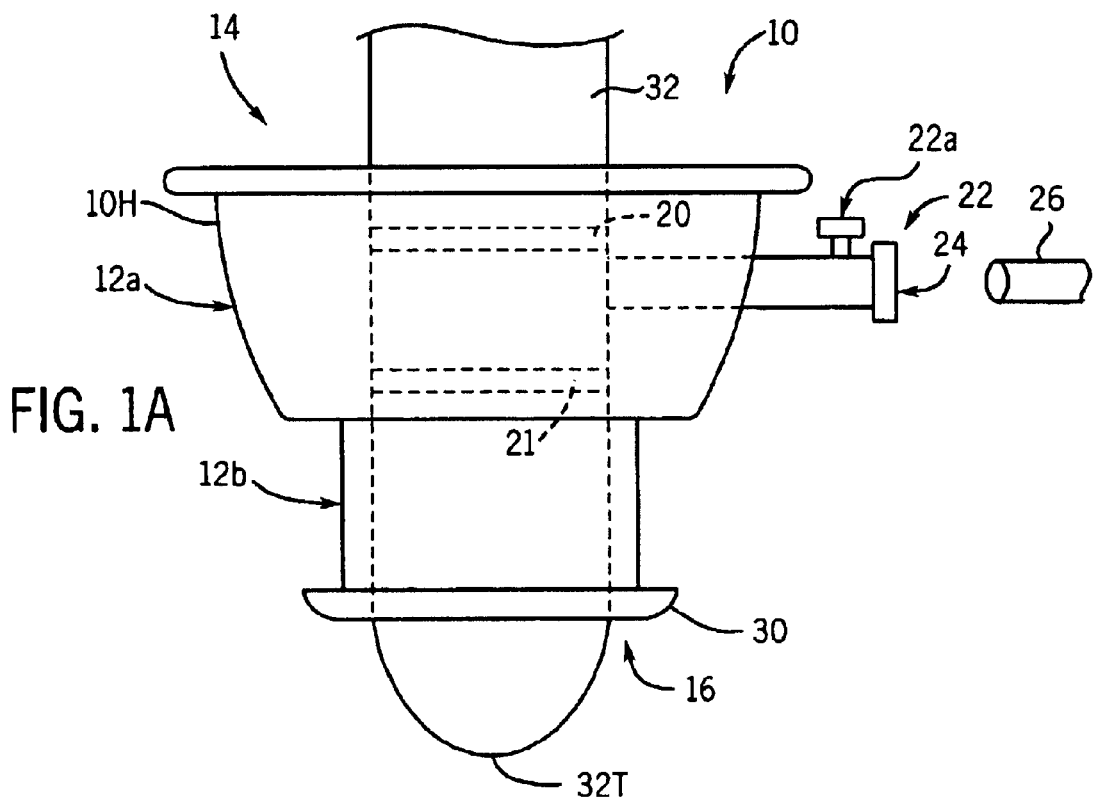
FIG. 1A is a side elevation view of the cardiac port of FIG. 1 with an obturator inserted therethrough.

With reference to the figures, wherein identical numerals indicate identical parts, and in particular to FIGS. 1 and 1A, a cardiac port, generally indicated 10, is shown. This cardiac port is configured for insertion through a chamber wall of a heart chamber to perform a medical procedure inside of a beating heart. The cardiac port 10 includes a housing 10H having a first end 14, a second end 16, and a lumen 18 extending therethrough between the first end 14 and the second end 16. During diagnostic and surgical procedures, medical instruments can be inserted through the lumen 18 and into the operative heart chamber, preferably the atria. Although the lumen 18 is shown having a uniform cross section, it will be understood that the lumen 18 can take various shapes and have a varied cross section. For example, the lumen can be wider at the first end 14 of the cardiac port 10 than at the second end 16.

The housing 10H is configured for insertion through a heart chamber wall, preferably an atrial wall, of a beating heart, as will be described in more detail below. When inserted, the first end 14 of the housing 10H remains exteriorly of the atrial wall, and the second end 16 is positioned interiorly of the atrial wall. The port 10 also includes at least one valve 20, and preferably two valves 20, 21, located in the housing 10H to open and close the lumen 18. The valves maintain a good seal against leakage of blood from, or air into, the heart chamber. The valves, which are shown schematically in FIGS. 1 and 1A, can be one-way valves. These valves 20, 21 allow instruments to pass through the lumen 18, but prevent blood from leaking out of the lumen 18 and air from going into the heart chamber through the lumen 18. It is preferable that the valves 20, 21 fit snugly against differently sized and shaped instruments so that, regardless of the shape/size of the instrument passing through the port, introduction of air into, and leakage of blood from, the heart chamber will be minimized. In one embodiment, valve 20 nearer the first end 14 is a tight sealing valve that prevents air from leaking into the heart chamber, and valve 21 nearer the second end 16 is slightly looser than valve 20 and prevents blood from surging out of the heart chamber when a medical instrument or the like is passed through the lumen 18.

An inlet 22 can be connected to the housing 10H at a location proximate valve 20. Placement of the inlet 22 at this position is advantageous because any air in the heart chamber will rise to the most superior position, here, adjacent the valve 20. Air bubbles trapped at a location at the underside of the valve 20 can be drawn out through the inlet 22. In this regard, the inlet 22 has an inlet passage 24 that is in fluid communication with the lumen 18 of the housing 10H. The inlet 22 also has a de-airing/blood infusing stopcock 22a that can be manually actuated to either allow air to flow out of the heart chamber or allow blood to be infused into the heart chamber. In this regard, the inlet 22 is configured to transmit a fluid either from exterior of the port 10 to the lumen 18 of the housing 10H or from the lumen 18 to exterior of the port 10.

A fluid transport device 26, such as a catheter or other fluid line, can be releasably attached to the inlet 22 at one end thereof. The other end of the catheter 26 can be attached to a fluid source, and a fluid channel extending between the ends of the catheter 26 passes fluid from the fluid source to the inlet 22. The fluid then can pass from the inlet 22 through the inlet passage 24 and through the lumen 18 into the heart chamber to maintain the intra-chamber pressure at a desired level. In one embodiment, the other end of the catheter 26 is inserted into an artery of the patient. Arterial blood can pass through the fluid channel of the catheter 26 from the patient's artery, through the inlet passage 24 of the inlet 22, through the lumen 18 of the housing 10H, and into the heart chamber. Providing arterial fluid to the heart chamber in this manner ensures that the pressure of the chamber remains at a sufficient pressure level.

This pressurization of the heart chamber with arterial blood minimizes the risk of air induction when medical instruments are introduced into the heart chamber through the cardiac port 10. A major concern with placement of any device into the heart is the potential for induction of air, particularly into the left side of the circulation pathway. The air could be embolized, systemically leading to stroke, organ ischemia, and death. The atria normally are pressurized at 3–10 mmHg (i.e., 3–10 mmHg higher than atmospheric pressure), and, in disease states, they may be as high as 15–25 mmHg (i.e., 15–25 mmHg higher than atmospheric pressure). This supra-atmospheric pressure generally will create a column of blood in any device or cannula placed into the chamber, allowing the end of the cardiac port of the present invention to remain open and devices to be placed through it. Indeed, some early attempts at closure of atrial septal defects were done on the beating heart through an "atrial well." With deep respiration, however, and when blood has been lost to surgery, the pressure can become sub-atmospheric, and air will be drawn into the cardiac chamber. By shuttling blood from the high-pressure arterial system having a mean pressure of 60–80 mmHg (i.e., 60–80 mmHg higher than atmospheric pressure) to the atrium, the pressure in the atrium will always remain above atmospheric pressure, and the risk of drawing air into the atrium is reduced.

In some instances, it may not be necessary to pressurize the atrium with arterial blood. For those instances, the port 10 can be configured without an inlet 22, or, for ports 10 having inlets 22, the stopcock 22a can remain closed.

In the embodiment shown in FIGS. 1 and 1A, the housing 10H includes a first portion 12a and a second, narrower portion or neck 12b. The valves 20, 21 preferably are located in the first portion 12a, and the inlet 22 preferably connects to the first portion 12a. The cardiac port 10 can include additional valves (not shown) either in the first or second portions 12a, 12b. The neck 12b has a diameter than is smaller than the diameter of the first portion 12a. As shown in FIG. 1, the neck 12b is the part of the cardiac port 10 that extends through the heart chamber wall CW. When the cardiac port 10 is inserted through the heart chamber wall, it is important that the portion of the port 10 that extends into the heart chamber does not unintentionally contact heart tissue or heart valves or interfere with the beating of the heart. Accordingly, the neck 12b has a length that is substantially equal to or slightly greater than the chamber wall CW. The neck length will depend on which chamber the port is inserted through and at what angle. A preferred neck length can fall within the range of approximately 5 mm–1 cm. In addition, the neck 12b is preferably flexible to conform to movement of the chamber wall CW as the heart beats. The right and left atria, which are the envisioned placement sites of the cardiac port of the present invention, have very thin walls. The flexibility of the neck 12b ensures that trauma to these thin walls is kept as minimal as possible. Neck flexibility also makes it easy for a surgeon to move the first end 14 of the port 10 to a position that facilitates insertion of instruments through the port 10. In other embodiments, the neck is not flexible, but rather is rigid.

The port 10 preferably has first and second retainer members, such as annular flanges or surfaces created by shoulders of the housing, to retain the chamber wall CW therebetween. For example, the second end 16 of the port 10 can include an outwardly extending flange 30, preferably in the form of an annular ring. An upper surface 30U of the flange 30 and a lower surface 12LS of the upper portion 12 anchor the port 10 in place in the chamber wall CW. The flange 30 prevents inadvertent withdrawal of the port 10 from the chamber wall CW.

A cardiac port assembly of the present invention can include a removable closure element 32, such as an obturator, configured to pass through the lumen 18 of the cardiac port 10, as shown in FIG. 1A. The obturator 32 dilates the initial stab wound through the heart chamber so that the port can be pushed through the chamber wall CW. The obturator 32 has a length sufficient such that, when the obturator 32 is fully inserted into the cardiac port 10, a tapered tip 32T extends through the second end 16 of the cardiac port 10. During placement of the cardiac port 10 through the heart chamber wall CW, the obturator 32 gradually dilates the atrial incision and, at the same time, by occupying the lumen 18, prevents air from entering the heart chamber via lumen 18 in the port 10.

The port 10 preferably is made of a biocompatible, plastic material. The neck 12b can be made of flexible plastic material or DACRON, for example, to be more flexible than the remaining portions of the port 10. The cardiac port of the present invention can be manufactured in various sizes, depending on the size of the instruments to be inserted therethrough.

Figure 2:
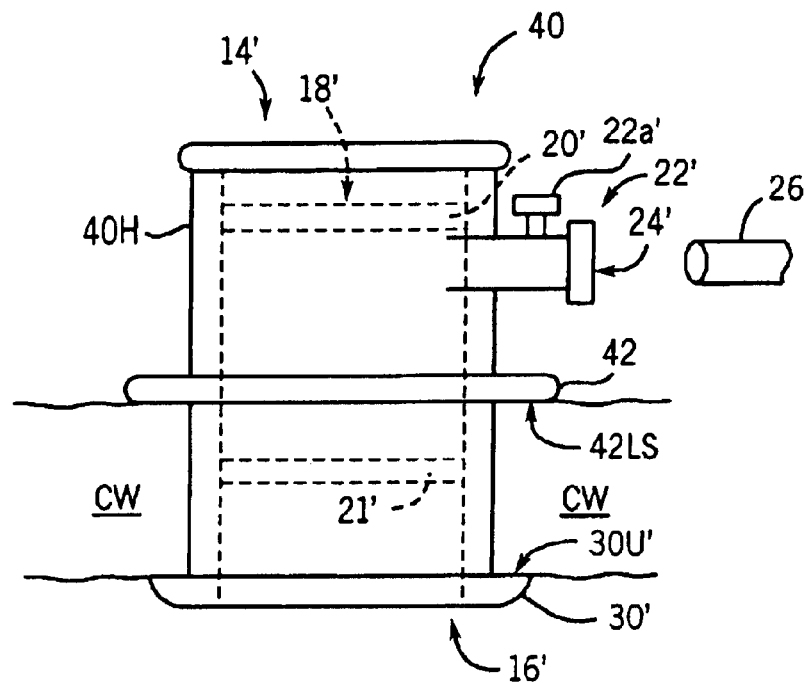
FIG. 2 is a side elevation view of a cardiac port in accordance with another embodiment of the invention.
Figure 2A:
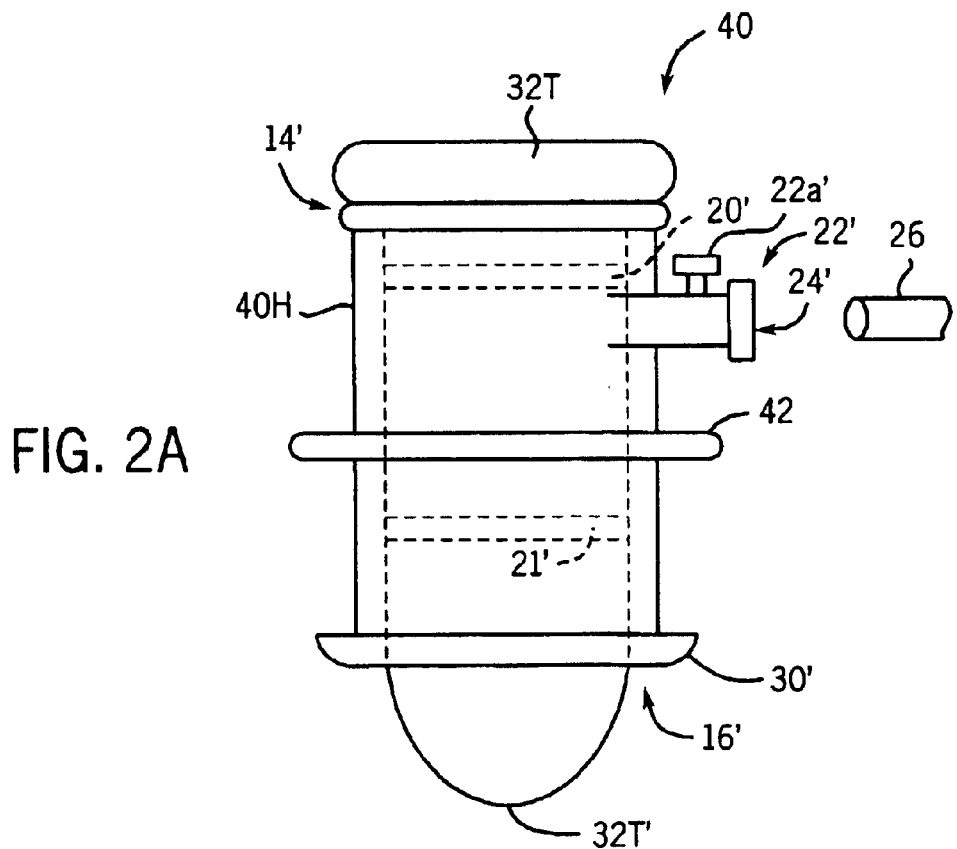
FIG. 2A is a side elevation view of the cardiac port of FIG. 2 with an obturator inserted therethrough.

FIGS. 2 and 2A show another embodiment of a cardiac port in accordance with the invention. The cardiac port 40 includes a housing 40H that is generally cylindrical in shape. The cylindrical body of this port 40, as compared to port 10, which has a larger diameter first portion 12a than second portion 12b, enables placement of a series of ports 40 or catheters through the chamber wall in relatively close proximity to each other. In addition, the smaller the diameter of the port 40, the more easily the port 40 can be tilted relative to the chamber wall CW. Also, the smaller the diameter of the port 40 (and hence the narrower the profile of the port 40), the more likely it is that the port 40 can be placed through the chamber wall CW using thoracoscopic techniques, instead of via a full thoracotomy.

The housing 40H has a first end 14', a second end 16', and a lumen 18' extending therethrough. The port 40 also includes at least one valve 20', and preferably two valves 20', 21', located in the housing 10H to open and close the lumen 18', as explained above in connection with the embodiment of FIGS. 1 and 1A.

An inlet 22' is connected to the housing 40H at a location proximate the valve 20', and the inlet 22' has an inlet passage 24' that is in fluid communication with the lumen 18' of the housing 40H. The inlet 22' also includes a de-airing/blood infusing stopcock 22a' that can be manually actuated to either allow air to flow out of the heart chamber or allow blood to be infused into the heart chamber. A fluid transport device 26, such as a catheter, can be releasably attached to the inlet 22' at one end and can be inserted into the artery of the patient at the opposite end to permit blood flow between the patient's artery and the heart chamber in the same manner as described above in connection with FIGS. 1 and 1A.

The housing 40H has a first flange 30' at the second end 16' of the housing 40 and a second flange 42 located on the housing at a location between the first and second ends 14', 16'. An upper surface 30U' of the first flange 30' and a lower surface 42LS of the second flange 42 anchor the port 40 in place in the chamber wall CW. The flange 30' prevents inadvertent withdrawal of the port 40 from the chamber wall CW. The length of the cardiac port 40 between the first and second flanges 30', 42, which extends through the chamber wall CW, can be made of a flexible material, like neck 12b in the embodiment of FIGS. 1 and 1A. In other embodiments, that length of the cardiac port 40 is made of an inflexible material.

In this embodiment, the second valve 21' can be positioned within the lumen 18' at a location between the first and second flanges 30', 42. Like in the embodiment of FIGS. 1 and 1A, the cardiac port assembly of FIGS. 2 and 2A can include a removable closure element 32', for example, an obturator, configured to pass through the lumen 18' of the cardiac port 40, as shown in FIG. 2A. This obturator 32' dilates the atrial incision and prevents air from entering the heart chamber during placement of cardiac port 40 into the chamber wall CW.

As mentioned above, during diagnostic and surgical procedures, medical instruments can be inserted through the lumen of the cardiac port. At the same time, arterial blood is shunted from the femoral artery, or other suitable artery of the patient, via a catheter attached to the inlet of the port. The arterial blood then is passed into the heart chamber via the inlet passage of the inlet and the lumen. By shunting the patient's own arterial blood into the inlet, the cardiac port efficiently keeps the pressure elevated in the heart chamber using the patient's circulation as a pressure/energy source.

Because the present invention involves performance of diagnostic and surgical procedures inside of a beating heart, and because these procedures are minimally invasive (as opposed to open heart procedures), the defect or chamber wall being evaluated or needing repair often is obscured by the patient's organs, tissue, and blood. Accordingly, the cardiac port of the present invention can be used in connection with imaging equipment for visualizing the beating heart during heart valve and septal defect surgery. The present invention contemplates repairing a beating heart using echocardiography or real-time CT scanning or magnetic resonance imaging (MRI) to "see" through the blood. Mitral valve repair, for example, can be performed on the beating heart, without the use of CPB, through a combination of next generation imaging techniques, endoscopic suture placement devices, and simplified valve repair techniques. According to the present invention, complex intracardiac and intravascular surgery can be performed on a closed chest patient under real-time three-dimensional imaging by robotic devices that are placed through the cardiac ports directly into the cardiac chambers.

Multiplane transesophageal echo cardiography (TEE), the current state of the art, has the capability of generating detailed two dimensional images of the mitral valve, including its leaflet edges and closure lines. (27; 28). TEE can provide accurate localization of regurgitant defects in the mitral valve. (29). Three dimensional echo imaging can provide even more detail, but that technique currently cannot be performed on the real-time basis required for surgical manipulation. (30). Advances in hardware and software suggest that this will be possible in the future, and the cardiac port of the present invention is designed to take advantage of these future advances in imaging technology.

In the past, standard mitral valve repair techniques involved resecting areas of redundant valve leaflets and mechanically reducing the valve annulus, thus improving leaflet edge coaptation to restore valve competence. The Alfiori method involves fixing the redundant section of a leaflet to the opposite valve edge. This recently described technique has been demonstrated to be effective and is technically simple enough to apply to the beating heart. The cardiac port of the present invention improves upon the Alfiori method by providing access to the mitral valve without the use of CPB.

Figure 5:
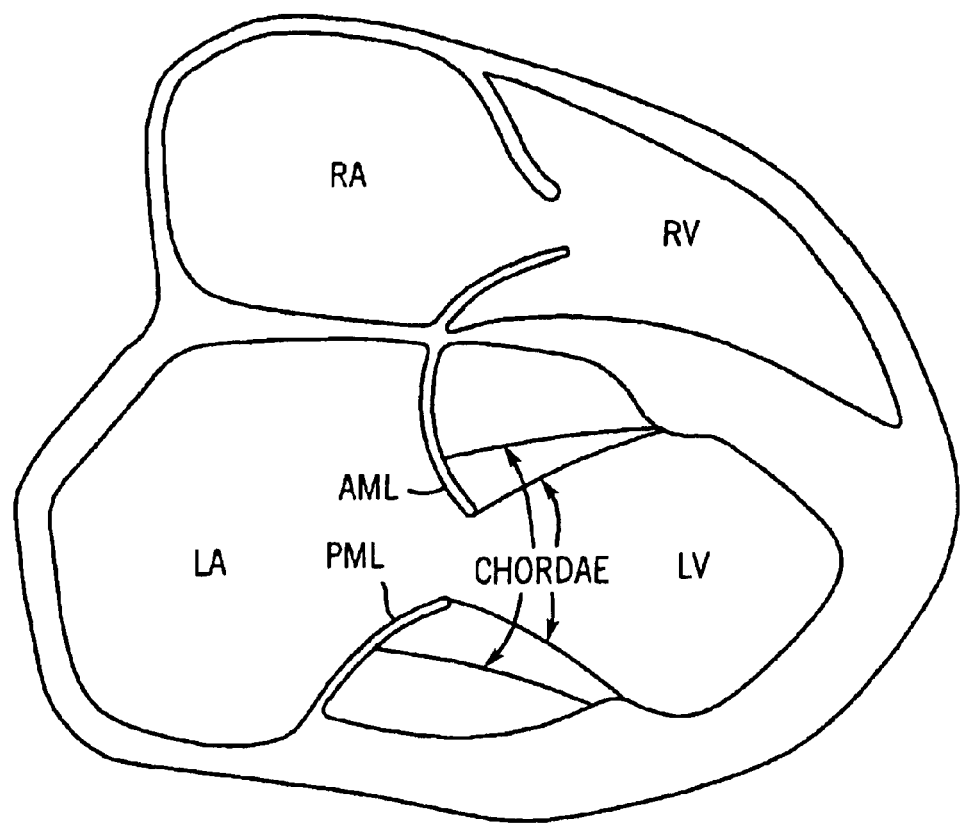
FIG. 5 schematically illustrates the anatomy of the heart.
Figure 6A:
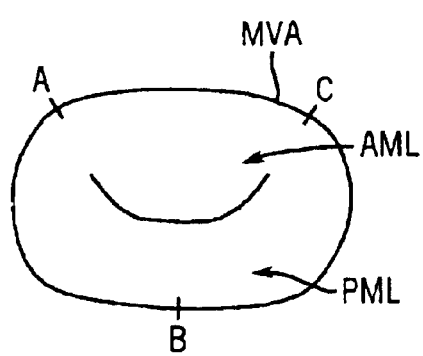
FIGS. 6A and 6B schematically illustrate the mitral valve, as seen from the left atrium.
Figure 6B:
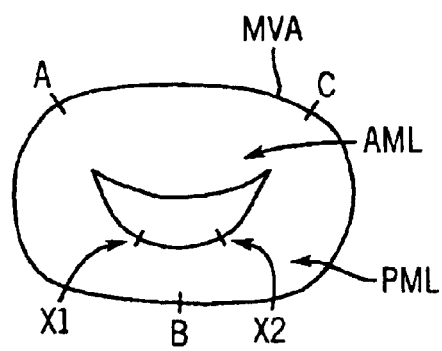

The cardiac port is designed to enable several standard surgical techniques to be performed as minimally invasive surgeries, including bow-tie repair, chordal replacement, and annuloplasty ring placement. The cardiac port of the present invention can be used to place sutures under the guidance of a standard TEE probe, and these sutures can be tied through the cardiac port. During surgical procedures, it is preferred that images be taken of a true short axis to provide the best working view of the mitral valve (short axis is shown in FIGS. 6A and 6B), with selected long axis views to orient the instruments within the heart chamber (long axis is shown in FIG. 5).

Figure 3A:
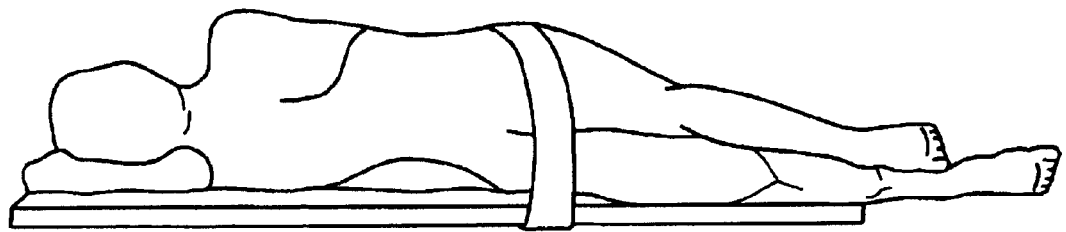
FIG. 3A schematically illustrates a patient placed in a right thoracotomy position.
Figure 3B:
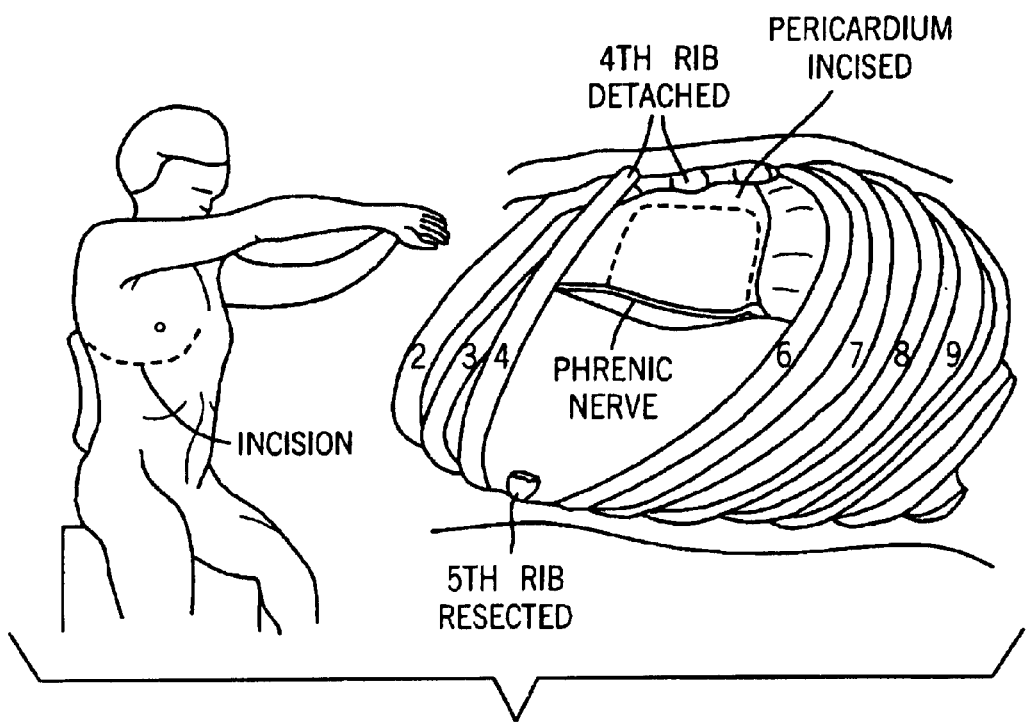
FIG. 3B schematically illustrates a right thoracotomy procedure.

A method of performing mitral valve repair in accordance with the invention will now be explained. As shown in FIG. 3A, the patient is placed in a right thoracotomy position, with the patient's left side down. This position minimizes the risk of drawing air in during the procedure. A right thoracotomy is performed, using single lung ventilation, as shown in FIG. 3B. The pericardium is opened and the left atrium exposed at the junction of the right pulmonary veins. Alternatively, the heart can be exposed in an identical manner utilizing thoracoscopic techniques, where the ports are placed using a thoracoscope. In all such techniques, low-dose systemic heparinization is utilized. It is envisioned that the below-described procedure can be used in the future with yet-to-be-developed suture placement devices, knot tying techniques, and other instrumentation, including robotic technology. For the present, the open-chest thoracotomy procedure can be used to perform mitral valve repair and other minimally invasive diagnostic and surgical procedures inside of a beating heart.

Figure 3C:
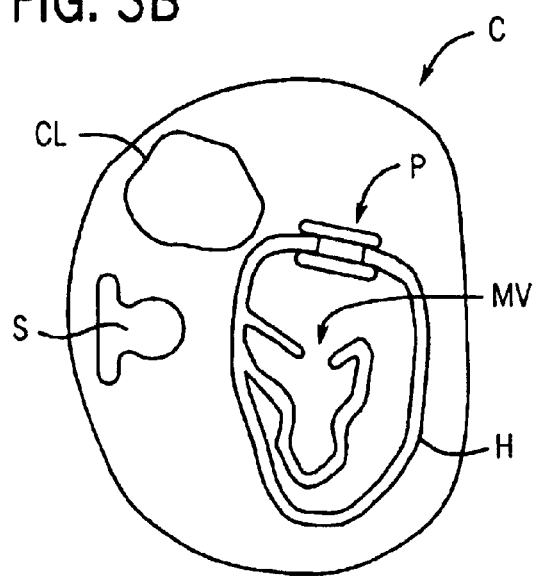
FIG. 3C schematically illustrates the patient's chest cavity C, as viewed in cross section, during a surgical procedure in accordance with the invention.
Figure 3D:
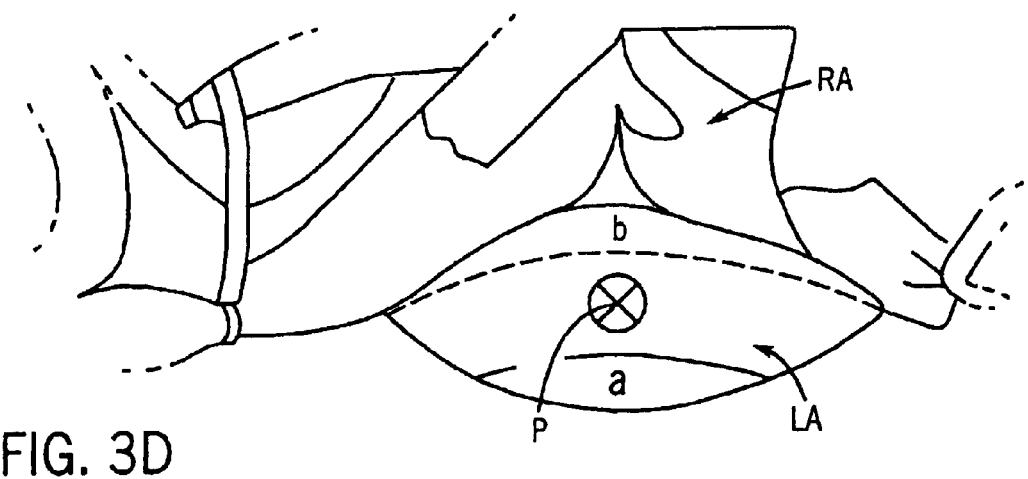
FIG. 3D schematically illustrates the heart, viewed in the direction of arrow A in FIG. 4, and shows one placement location of a cardiac port during a surgical procedure in accordance with the invention.

FIG. 3C is a schematic of the patient's chest cavity C, as viewed in cross section, during the surgical procedure. The patient's collapsed left lung CL, spine S, heart H, mitral valve MV, and preferred placement of the cardiac port P are shown in FIG. 3C. FIG. 3D illustrates the right and left atria RA, LA and the approximate placement of the cardiac port P through the chamber wall CW of the left atria LA during the thoracotomy procedure, which sets the stage for the mitral valve surgery in accordance with the invention.

Figure 4:
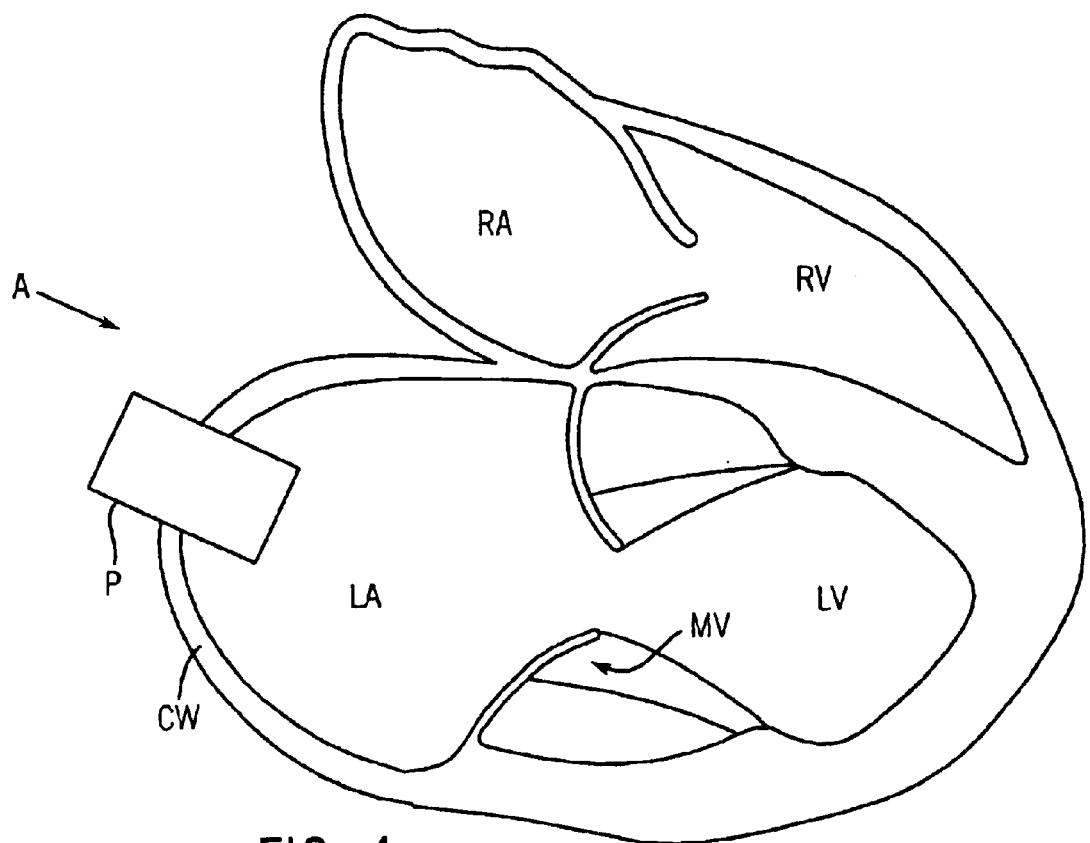
FIG. 4 schematically illustrates the anatomy of a heart and shows placement of a cardiac port through the chamber wall of the left atrium.

FIG. 4 illustrates the anatomy of the heart. Specifically, FIG. 4 shows the left atria LA, right atria RA, and mitral valve MV that separates the left atria LA and left ventricle LV. A block representing the cardiac port P is shown penetrating the chamber wall CW of the left atria LA. It will be understood that the port P shown in FIG. 4 and in the other figures is not necessarily to scale relative to the left atria LA. FIG. 5 also shows the anatomy of the heart. As best seen in FIG. 5, the mitral valve MV includes an anterior mitral leaflet AML and a posterior mitral leaflet PML.

FIGS. 6A and 6B schematically illustrate the mitral valve along its short axis, as seen from the left atrium. FIG. 6A shows a normal mitral valve in a closed position. FIG. 6B shows a leaking mitral valve. Encircling the mitral valve is the mitral valve annulus MVA. The mitral valve annulus is the structure that makes up the circumference or ring around the mitral valve. The anterior mitral annulus is defined as that portion of the mitral valve annulus from A to C. The posterior mitral annulus is defined as that portion of the mitral valve annulus from A to B to C. Leaking of the mitral valve can occur due to a torn chordea (labeled X1 and X2 in FIG. 6B, labeled chordea in FIG. 5). Leaking can also occur due to dilation of the posterior mitral annulus. When the posterior mitral annulus dilates, the mitral valve leaflets no longer properly come into contact with one another, and the mitral valve leaks.

Figure 7:
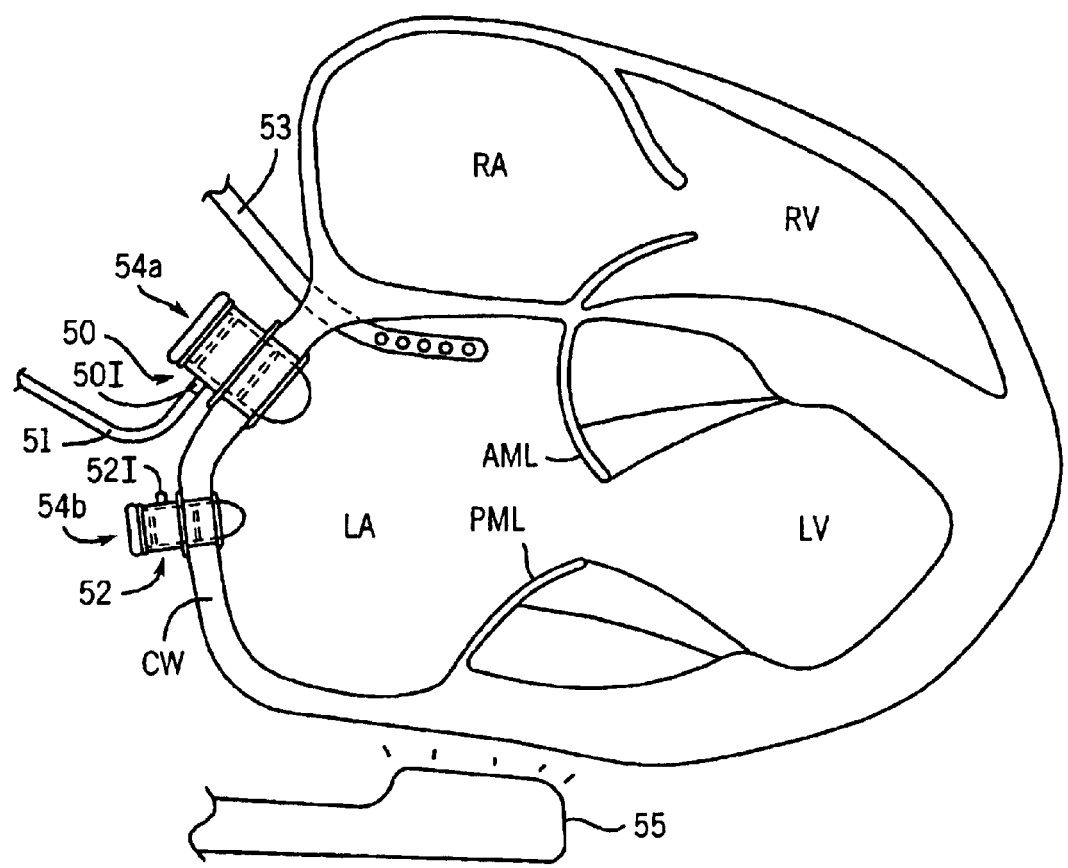
FIG. 7 schematically illustrates cardiac ports and obturators inserted through the chamber wall of the left atrium in preparation for a surgical procedure in accordance with the invention.

Turning now to FIG. 7, two cardiac ports 50, 52 are shown inserted through the chamber wall CW of the left atrium LA. The ports 50, 52 have the configuration of port 40 in FIGS. 2 and 2A, but it will be understood that ports having a different exterior configuration, such as that shown in FIGS. 1 and 1A, can be used in this surgical technique. Prior to their insertion through the chamber wall CW, the ports 50, 52 are saline primed via their inlets 50I, 52I to remove all air from the central lumens of the ports 50, 52. Port 50 serves as a main working port. Port 52 is optional and, if inserted through the chamber wall CW, can serve as an auxiliary port to allow passage of a second set of instruments into the heart chamber.

Figure 8:
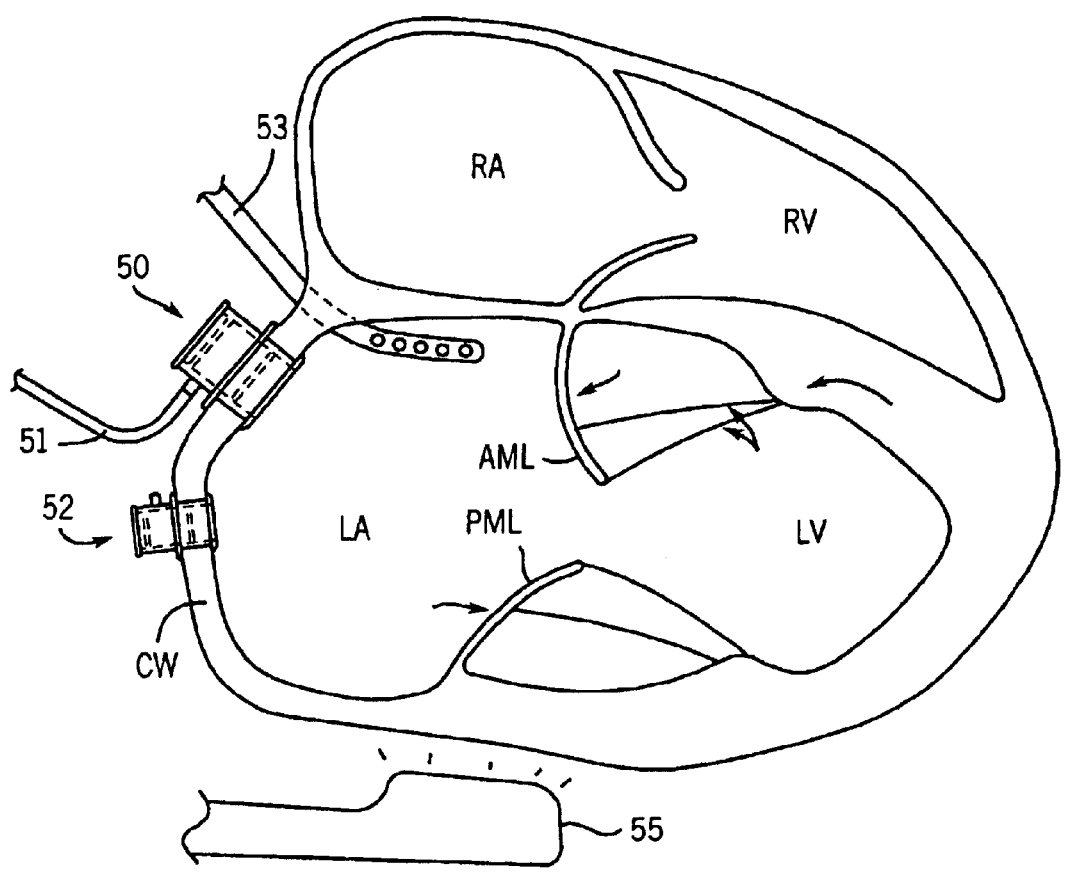
FIG. 8 schematically illustrates cardiac ports inserted through the chamber wall of the left atrium in preparation for a surgical procedure in accordance with the invention.

To insert ports 50, 52, a pursestring suture is placed into the chamber wall CW at a desired entry point, and a stab wound is made in the center of the suture. The port and its obturator are then pushed through the stab wound. Once the ports 50, 52 are positioned in place in the chamber wall CW, the respective obturators 54a, 54b are removed, and the ports are de-aired via the stopcocks of their inlets 50I, 52I. One end of a line 51, such as a catheter, is attached to the inlet 50I of port 50, and the other end of line 51 is inserted percutaneously into a peripheral artery of the patient, such as the femoral artery (not shown). Blood flow through the line 51 and into the port 50 is adjusted by a variable occluder to maintain an atrial pressure of greater than 20 mmHg (i.e., 20 mmHg higher than atmospheric pressure). A variable occluder can include an adjustable clamp to regulate flow. A more sophisticated variable occluder can incorporate a pressure regulating device to keep the atrial pressure from rising to more than, for example, 25 mmHg (i.e., 25 mmHg higher than atmospheric pressure). Atrial pressure is transduced, or measured, through a fluid-filled line 53 placed into the most superior portion of the atrium. This line 53 also functions as another de-airing portal when low manual suction is applied to it. FIG. 8 shows a cannulated heart. In an alternative embodiment, a cannula or small tube can be positioned through the chamber wall, and the heart chamber can be pressurized by shunting arterial blood from the patient's artery into the heart chamber via the cannula.

Depending on the patient's morphology, either a transesophageal probe, such as probe 55 in FIG. 7, inserted in a standard fashion in the patient's esophagus can be used to image the patient's heart during the surgical procedure, or a sterile echo probe can be inserted directly into the pericardium beneath the heart in the space between the superior and inferior pulmonary veins. As real-time three-dimensional echo, CT and MRI systems become available for operating room use, these will likely supplant TEE as the sole imaging modality.

After identifying the anatomic structures on echo, and assessing the cause of the mitral valve dysfunction, repair is undertaken, as illustrated in FIGS. 9–14. Stenotic mitral valves with commisural fusion, where the valve leaflets fuse together, causing the valve opening to become narrow or "stenose," are manually fractured with a spreading device placed through the port under direct echo guidance. The spreading device, for example, endoscopic scissors, force the valve leaflet edges apart. Regurgitant valves, i.e., valves which regurgitate blood from the ventricle to the atrium, will be treated in the following manner.

Figure 9:
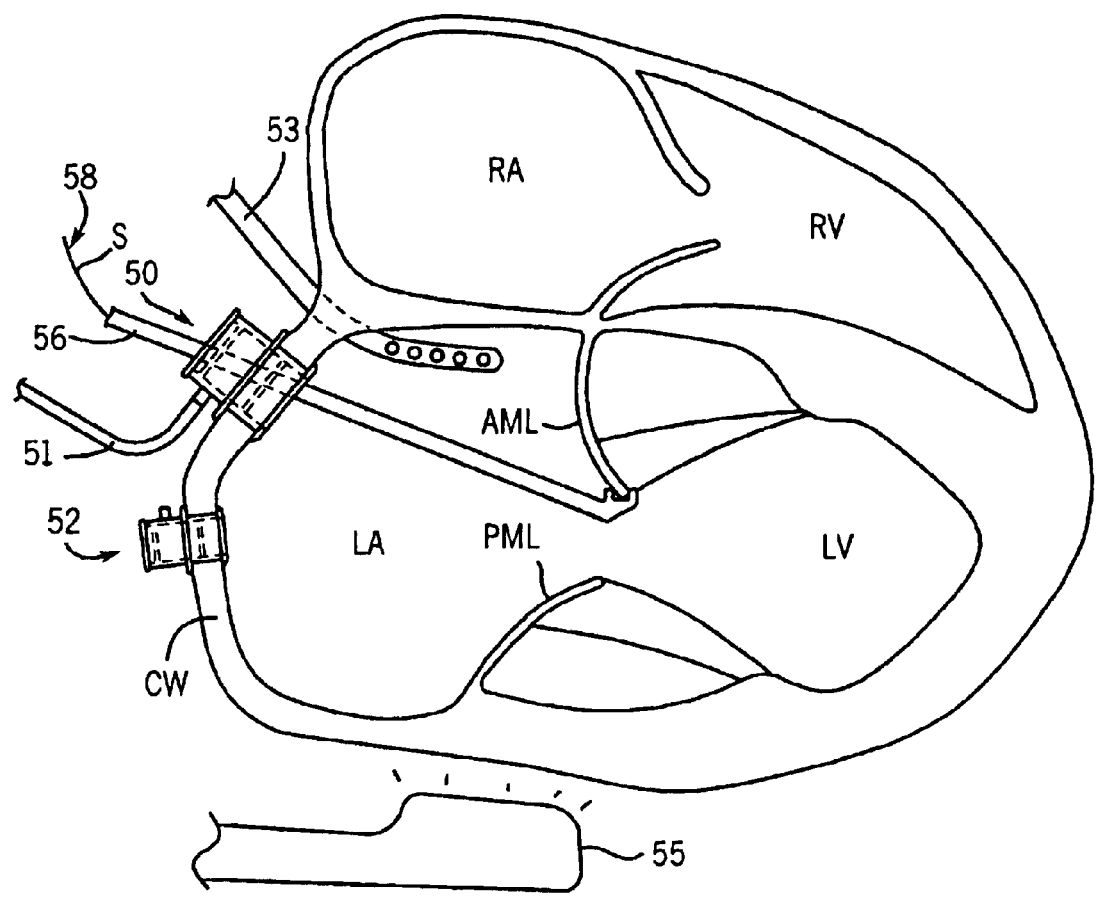
FIG. 9 schematically illustrates an endoscopic suture placing device inserted through a cardiac port.
Figure 9A:
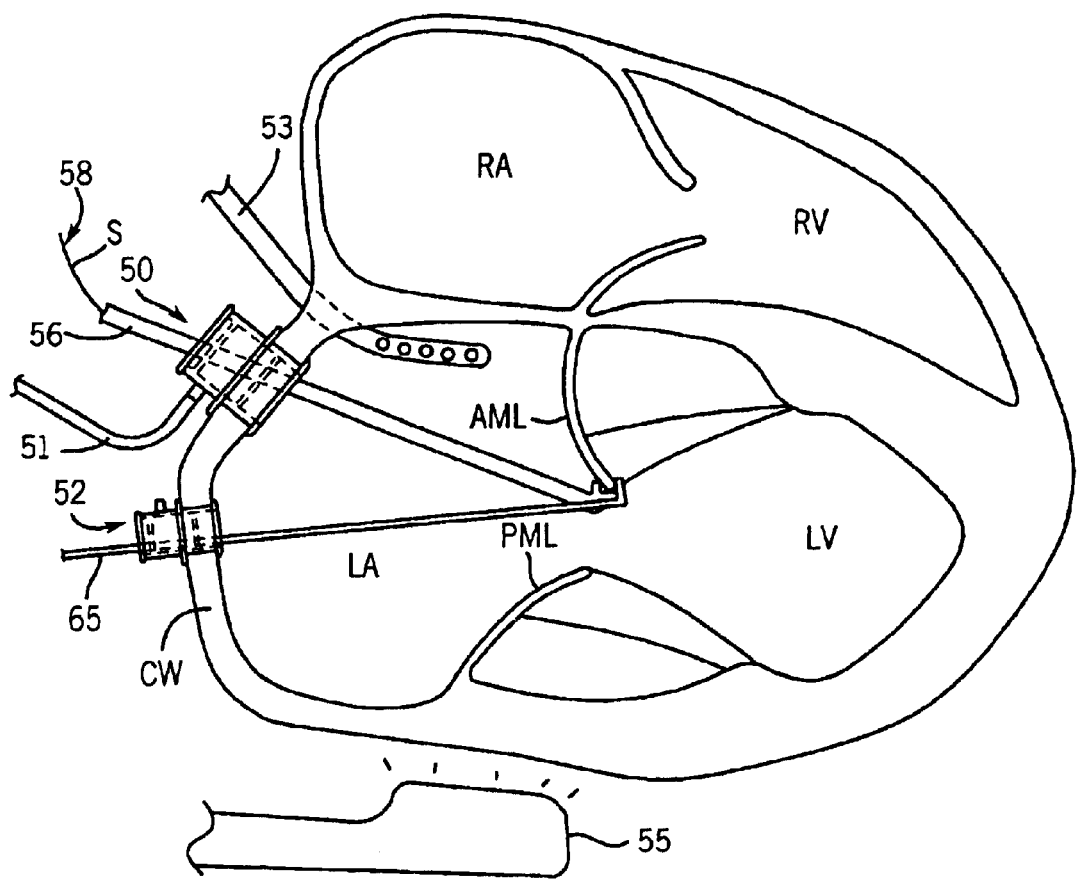
FIG. 9A schematically illustrates an endoscopic suture placing device inserted through a first cardiac port and a stabilizing device inserted through a second cardiac port.
Figure 9B:
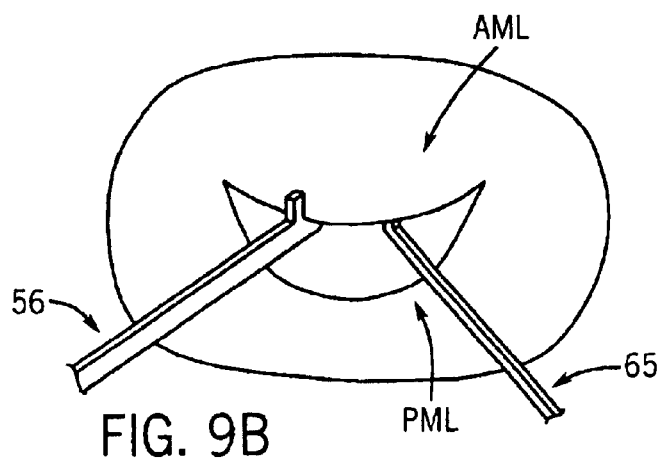
FIG. 9B schematically illustrates a mitral valve, where one leaflet of the mitral valve is engaged by an endoscopic suture placing device and a stabilizing device.

Referring to FIG. 9, an endoscopic suture placing device 56 is inserted through the main working cardiac port 50. If needed, a customized valve hook device and/or grasper device 65, as shown in FIGS. 9A and 9B, can be inserted through the second port 52 to stabilize the valve leaflets AML, PML and to facilitate suture placement by the suture placing device 56.

Figure 10:
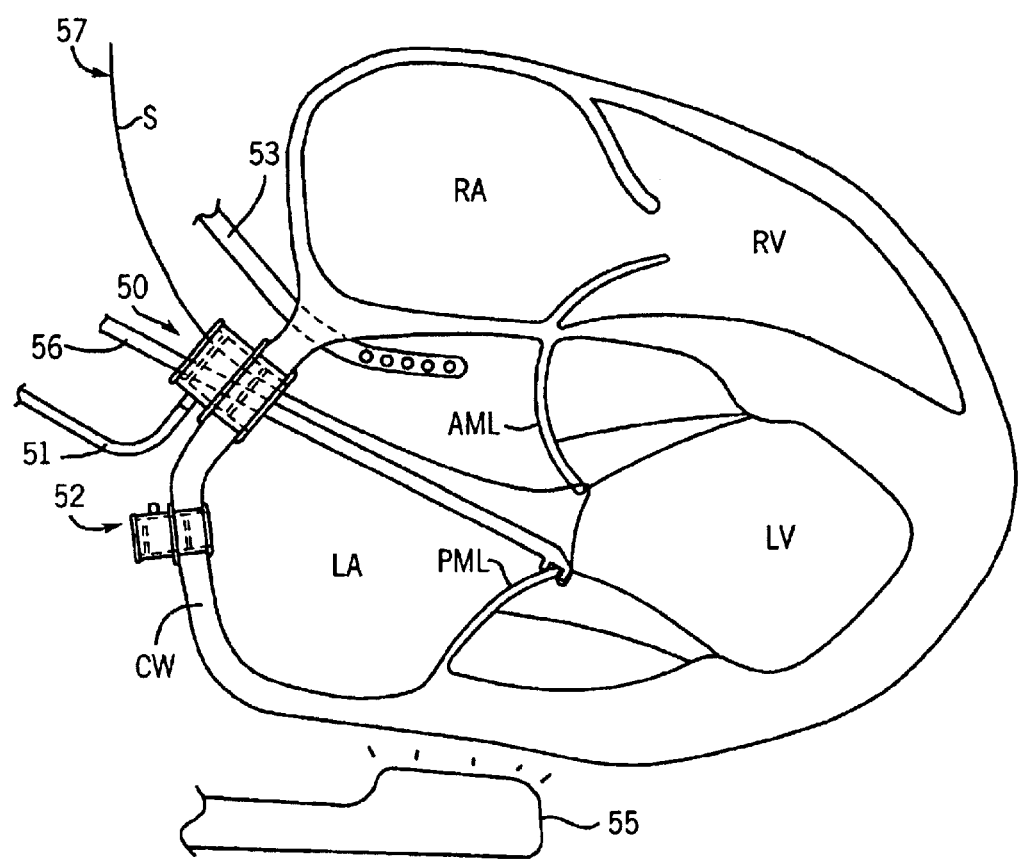
FIG. 10 schematically illustrates suture placement in anterior and posterior leaflets of the mitral valve by an endoscopic suture placing device.

The suture has needles at both ends 57, 58. One end of the suture S remains outside of the patient's body under the control of the surgeon at all times to minimize the risk of the suture getting loose in the patient's circulatory system. FIG. 9 shows the needle on suture end 57 (obscured by device 56) being placed through the anterior mitral leaflet AML, with suture end 58 remaining outside of the patient's body. FIG. 10 shows the needle on suture end 58 (obscured by device 56) being placed through the posterior mitral leaflet PML, with suture end 57 remaining outside of the patient's body.

Figure 11:
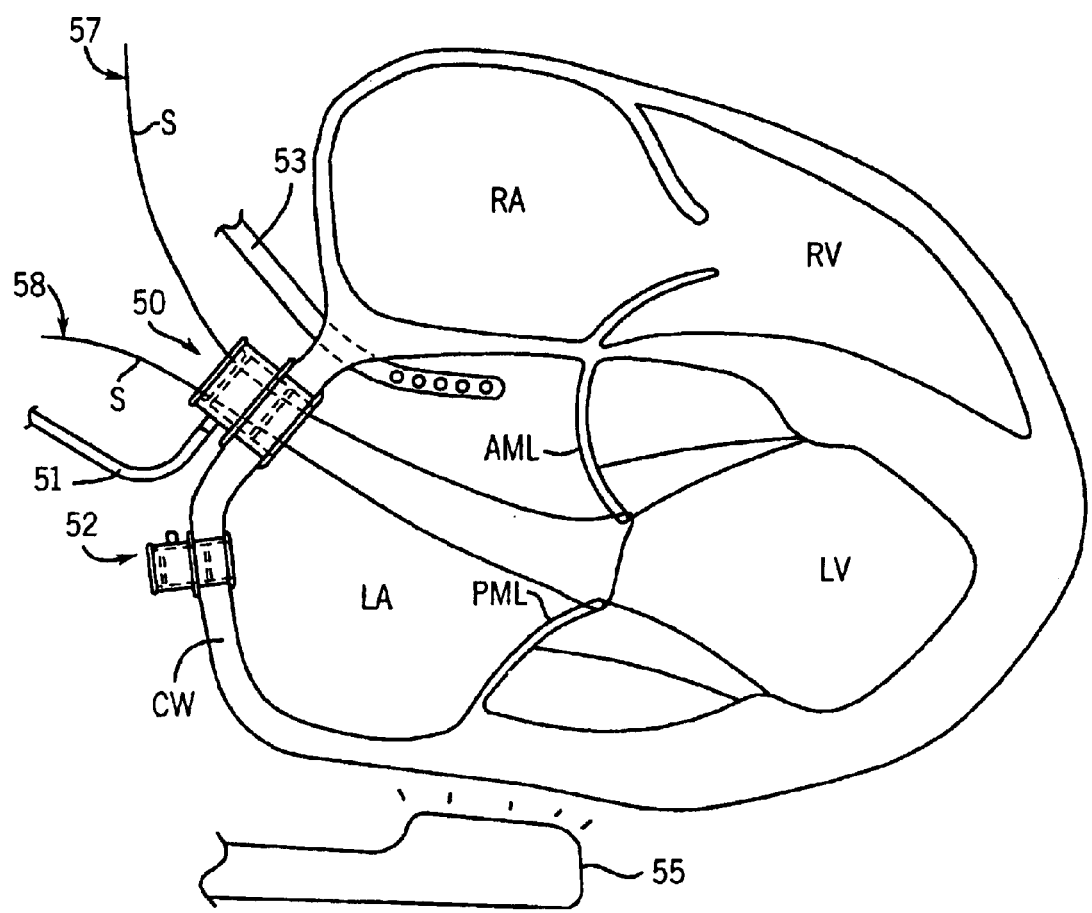
FIG. 11 schematically illustrates suture location relative to the mitral valve and the cardiac port, following placement of the suture by an endoscopic suture placing device.

To properly place the suture in FIG. 9, the suture placing device 56 grasps the anterior leaflet AML at its free edge (the whole procedure being done under echo guidance) and fires the suture S through the anterior leaflet AML. The end 57 of the suture S that has just been fired through the anterior leaflet AML then is brought out of the left atrium LA by the suture placing device 56 via the port 50. Next, end 58 is loaded into the suturing device 56, and the suture placing device 56 is fed back through the port 50 and into the left atrium LA. The appropriate section of the posterior leaflet PML then is grasped by the suture placing device 56, and the suture end 58 is fired through the posterior leaflet PML, as shown in FIG. 10. This end 58 of the suture S too is brought out through the port 50, as shown in FIG. 11.

Figure 12:
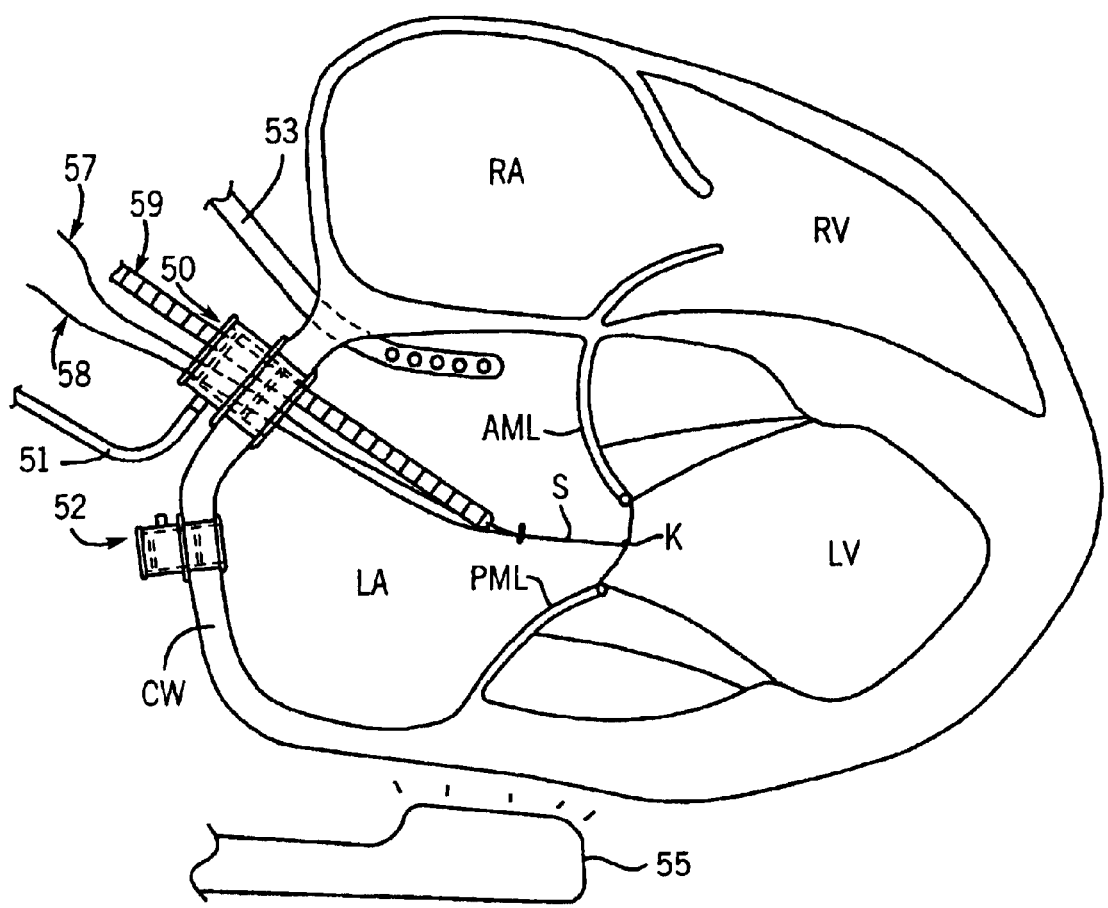
FIG. 12 schematically illustrates insertion of an endoscopic knot pusher through a cardiac port, where the endoscopic knot pusher ties off the suture through the mitral valve.

At this stage of the procedure, the suture S has two suture arms that terminate at ends 57, 58 outside of the port 50. The suture S is tied using a standard endoscopic knot pusher 59, as shown in FIG. 12.

Figure 13:
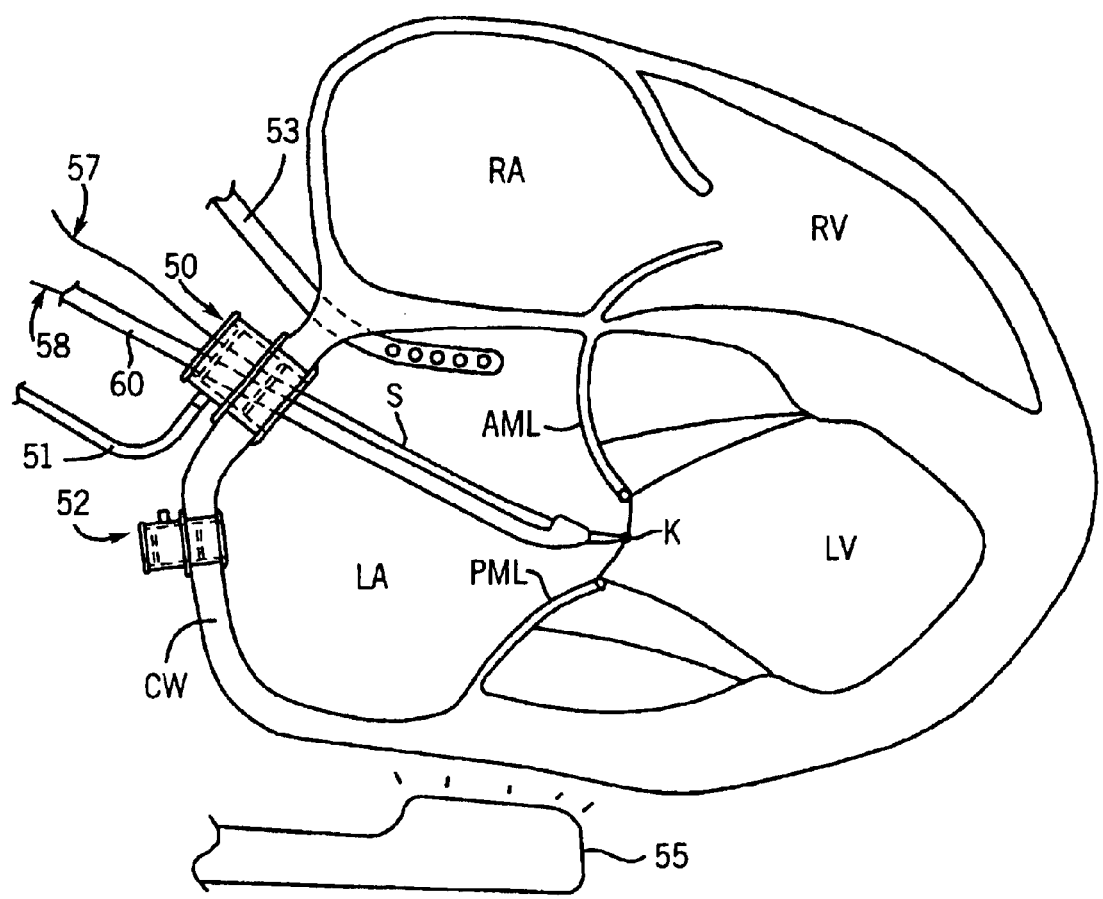
FIG. 13 schematically illustrates insertion of a suture cutting device through a cardiac port, where the suture cutting device cuts the suture.
Figure 14:
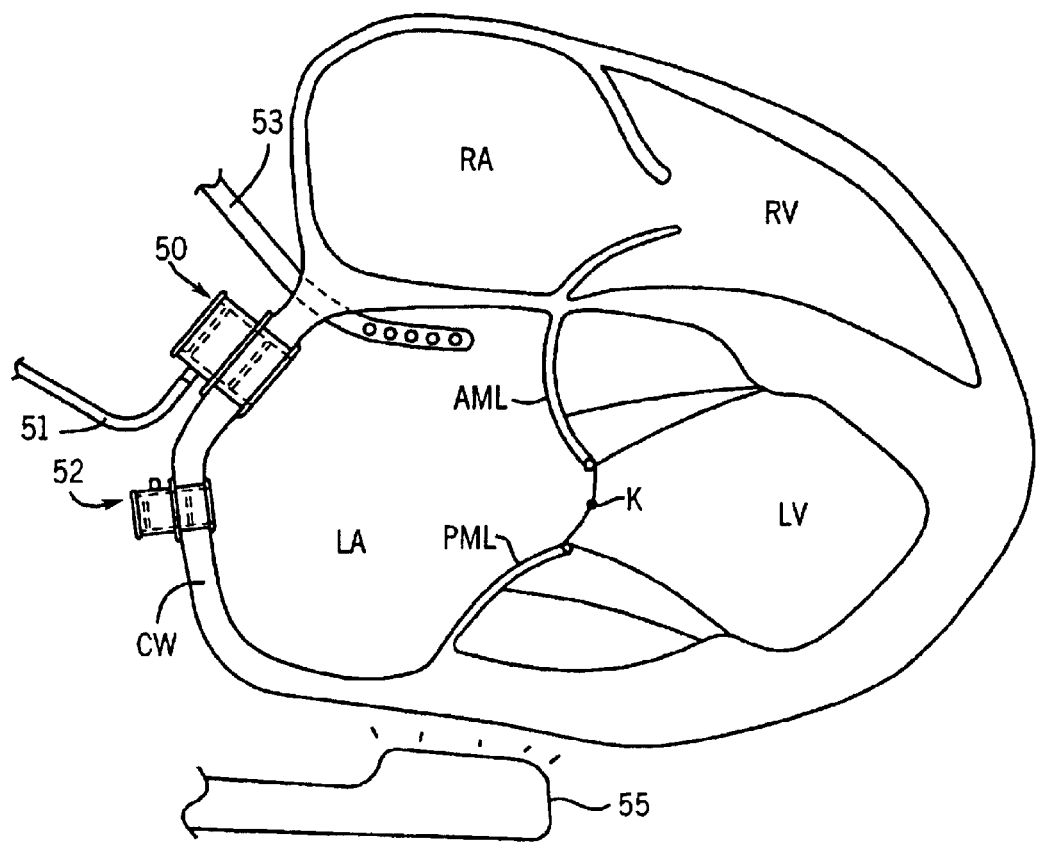
FIG. 14 schematically illustrates the anterior mitral leaflet and the posterior mitral leaflet sutured together.
Figure 16:
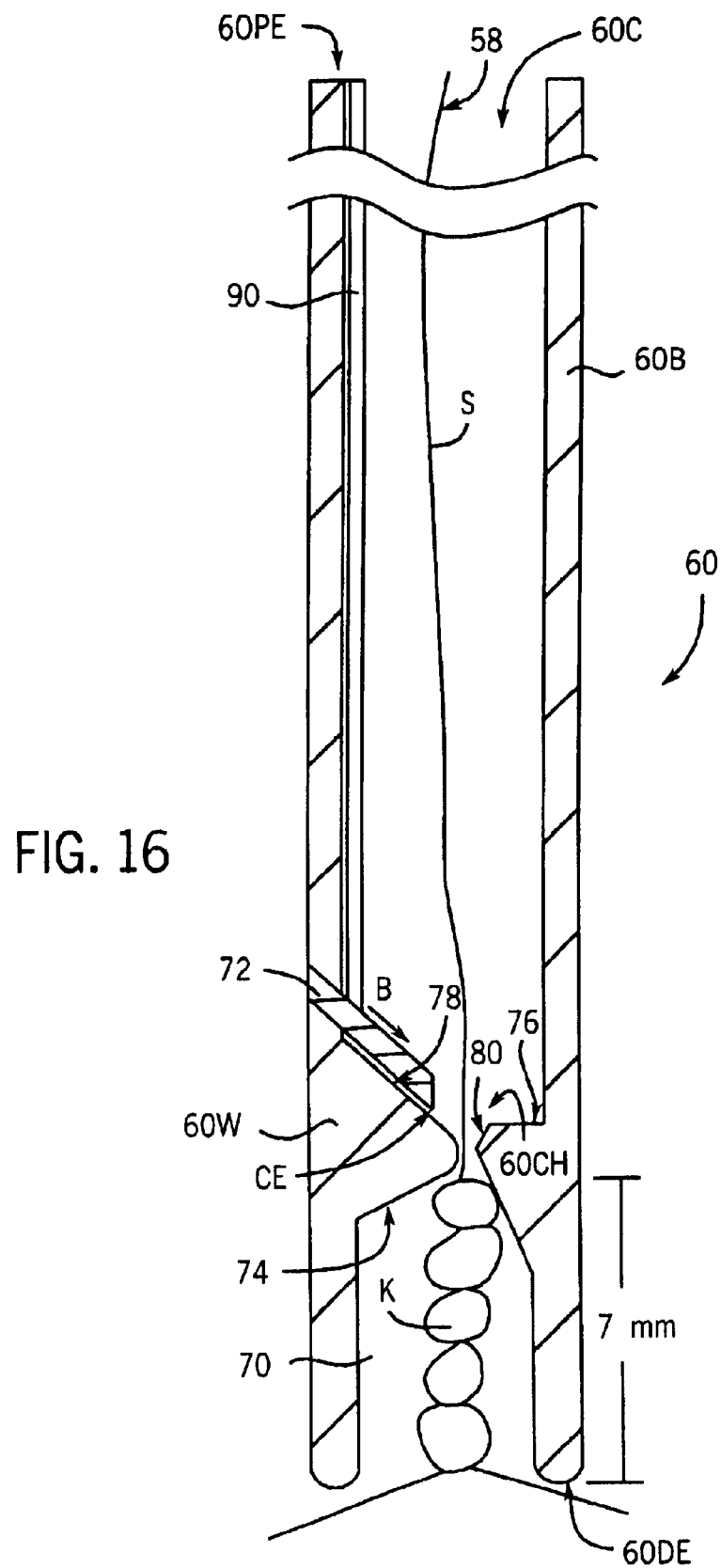
FIG. 16 is a side elevation view of a suture cutting device in accordance with the invention.

A suture cutting device 60 of the present invention is then run down one arm of the suture S, and the excess suture is trimmed, as shown in FIG. 13. In FIG. 13, suture end 58 is shown extending from the suture cutting device 60. The device 60 runs down over the suture arm S to avoid cutting other structures and is designed to cut each suture arm S at least 7 mm from the leaflets AML, PML, retaining a tail of at least 3 mm. This procedure avoids accidentally cutting the knot K. The suture cutting device 60 is illustrated in FIG. 16 and will be described more fully below. This suture cutting procedure is repeated down the other suture arm. Tying off the suture S in this manner leaves the central portions of the anterior and posterior mitral leaflets AML, PML sewn to one another in the manner of an Alfiori or "bow-tie" mitral valve repair, as seen in FIG. 14 and as is done in conventional open heart surgery. It will be understood that multiple sutures can be placed through the mitral leaflets, if necessary.

In a preferred embodiment of the invention, the suture cutting device 60 is run down on suture arm at a time to reduce the chance of the knot K being cut. However, it will be understood that, in an alternative embodiment, the suture cutting device can be run down both suture arms at the same time, and both suture arms then would be cut at the same time.

Once the suture has been tied off, the cardiac ports 50, 52 are then removed, and the wounds in the chamber wall CW and tissue are closed in standard fashion. This entire mitral valve repair procedure is performed on a beating heart; CPB is not employed.

Figure 15A:
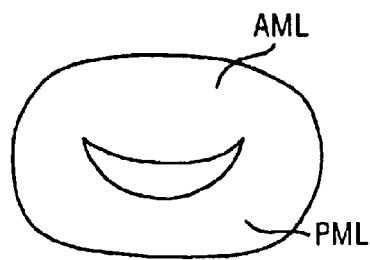
FIG. 15A schematically illustrates a damaged mitral valve, viewed from the left atrium.
Figure 15B:
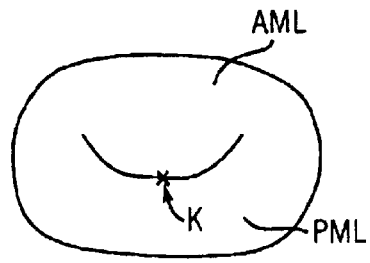
FIG. 15B schematically illustrates a repaired mitral valve, viewed from the left atrium.

FIGS. 15A and 15B show the mitral valve before and after the above-described surgical procedure. FIG. 15A shows a damaged mitral valve, where the leaflets AML, PML leak, and FIG. 15B shows the mitral valve in its repaired state following the surgical procedure.

Figure 17:
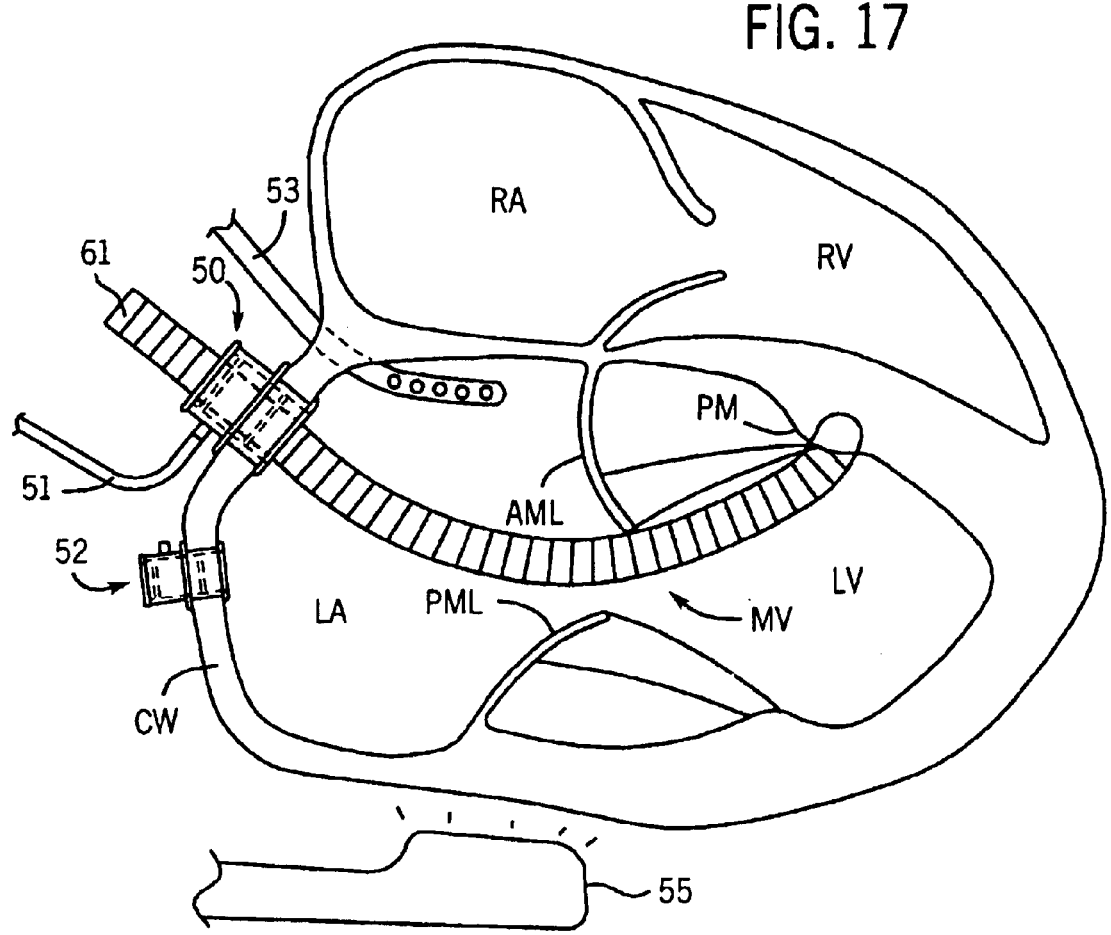
FIG. 17 schematically illustrates a curved suture placement device inserted through a cardiac port to replace a chordea of the mitral valve.

The cardiac ports of the present invention can be used in other surgical procedures. For example, if resecurement of one of the chordae to the papillary muscle PM of the ventricle is needed, a curved suture placement device 61 can be inserted through the lumen of port 50 and placed across the mitral valve MV, as shown in FIG. 17. The suture placement device 61 then can be fired into the papillary muscle PM. The free ends of the suture then can be brought through the edge of the operative mitral leaflet (here, in FIG. 17, the anterior mitral leaflet, although, in reality, it is usually the posterior mitral leaflet having the torn chord), as described above in connection with FIGS. 10–14.

Figure 18:
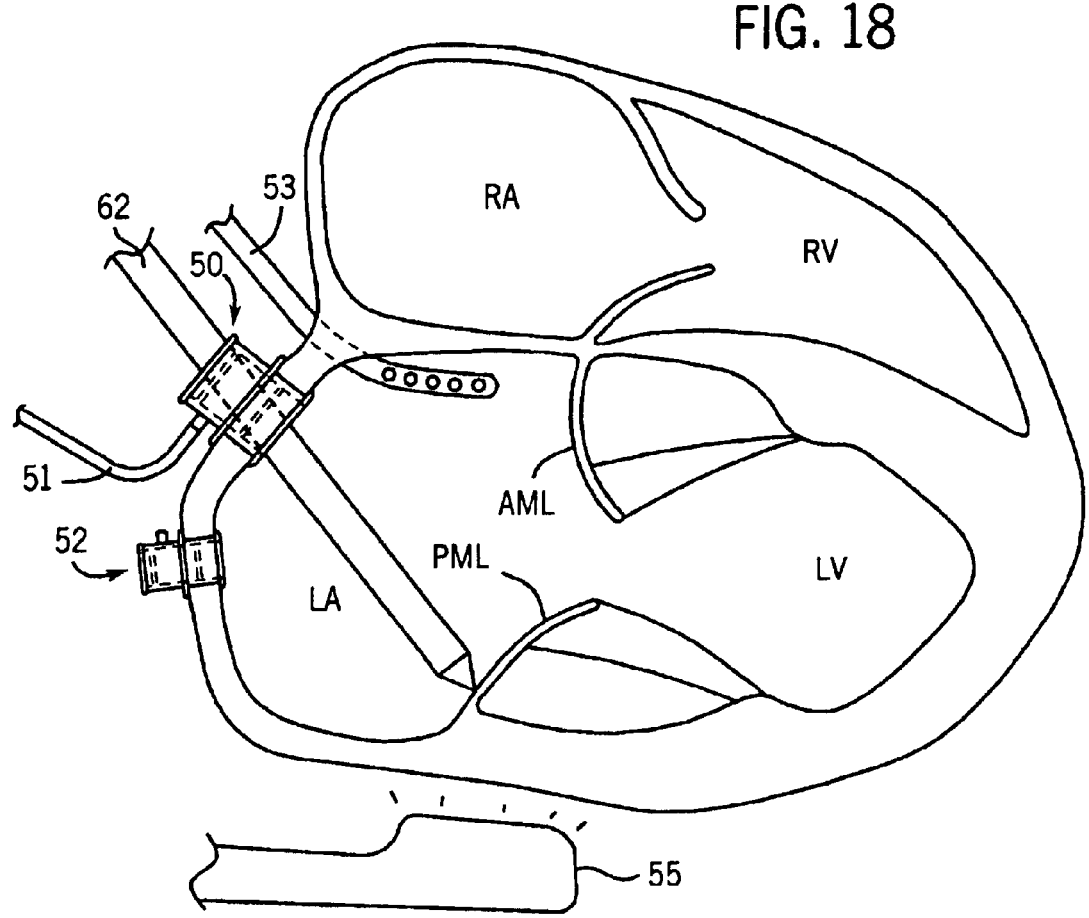
FIG. 18 schematically illustrates a stapling device inserted through a cardiac port during a stapled annuloplasty procedure in accordance with the invention.
Figure 19A:
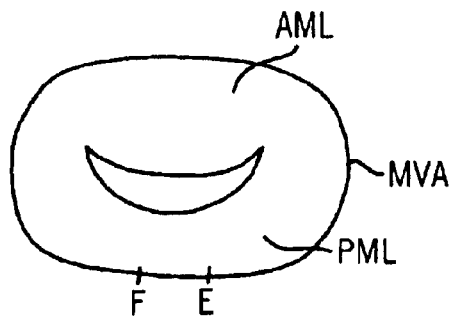
FIG. 19A schematically illustrates a damaged mitral valve prior to stapling, viewed from the left atrium.
Figure 19B:
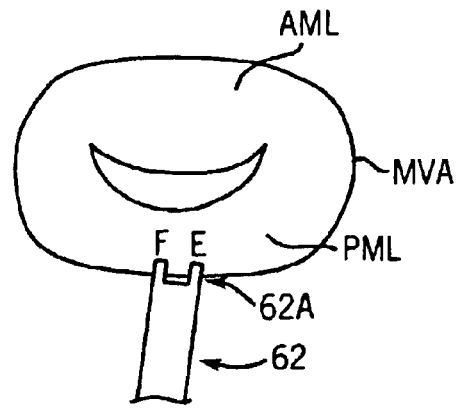
FIG. 19B schematically illustrates introduction of a stapling device toward a damaged mitral valve, viewed from the left atrium.
Figure 19C:
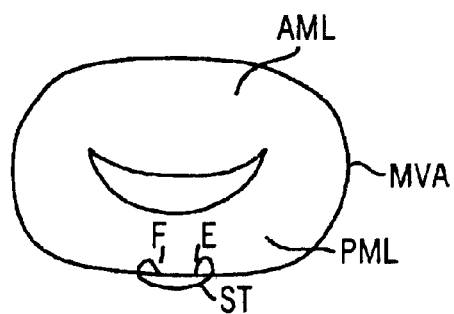
FIG. 19C schematically illustrates a staple placed in the posterior mitral leaflet, which shortens the mitral leaflet at the staple location, viewed from the left atrium.
Figure 23A:
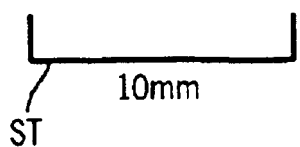
FIG. 23A schematically illustrates a staple prior to firing from a stapling device.
Figure 23B:
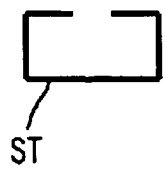
FIG. 23B schematically illustrates a staple after firing from a stapling device.
Figure 19D:
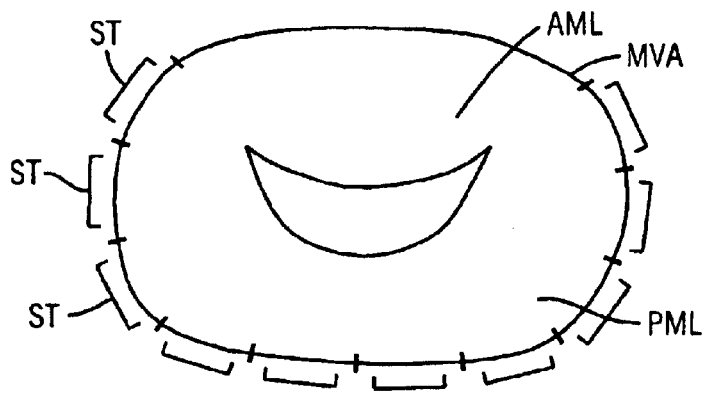
FIG. 19D schematically illustrates a damaged mitral valve and staple placement, viewed from the left atrium.
Figure 19E:
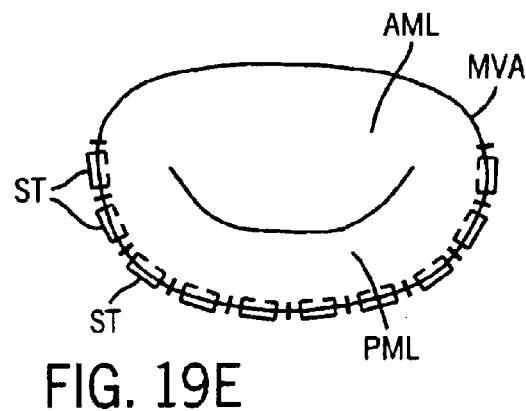
FIG. 19E schematically illustrates a repaired mitral valve after to stapling, viewed from the left atrium.

In another example, if a reduction in the posterior mitral annulus is needed to supplement the repair, a stapled annuloplasty can be performed in accordance with the invention. In the stapled annuloplasty procedure, a stapling device 62 is placed through the cardiac port 50, as shown in FIG. 18. A row of staples ST is fired along the posterior mitral annulus, running from the left to the right fibrous trigones (approximately at A and C in FIGS. 5A and 5B). The staples reduce the length of the posterior mitral annulus. The staples ST from the device 62 cover a distance of 10 mm when first pushed into the mitral annulus, as shown in FIG. 23A. Firing the device 62 causes the staples ST to fold in on themselves, as shown in FIG. 23B. This is shown in FIGS. 19A–19E. Points E and F in FIG. 19A are 10 mm apart before staple firing. Points E and F are 5 mm apart afterwards, as shown in FIG. 19C. By varying the size of the anvil 62A in the tip or head of the stapling device 62, seen in FIG. 19B, varying amounts of folding will occur in the staple during firing. The greater the amount of folding that occurs in the staple, the greater the amount of tissue plication that will occur. In one embodiment, for example, the staples ST fold from 10 mm to 7 mm, and, in a second embodiment, the staples ST fold from 10 mm to 5 mm. The staple size and the anvil head size can be varied to change the amount of plication that occurs with staple firing. Referring to FIGS. 19D and 19E, the staple placement can lead to a 30–40% reduction in the length of the posterior mitral annulus, as observed in conventional hand-sewn mitral annuloplasty. The stapling device 62 can be made in two types in accordance with the invention, one with individual staples, and one with staples that are connected to one another by a suture or band of material such as DACRON. This connection between staples may help to prevent delayed dilation of the annulus in the spaces between the sutures.

Figure 20A:
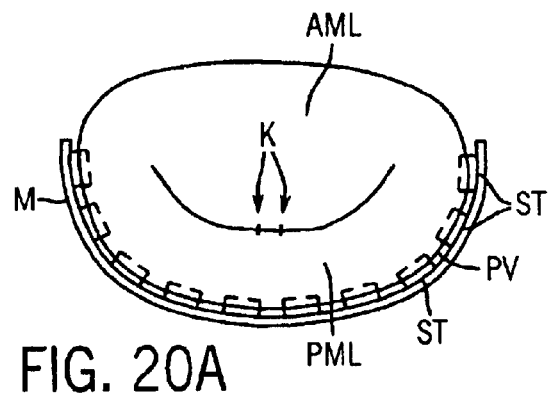
FIG. 20A schematically illustrates a repaired mitral valve during systole.
Figure 20B:
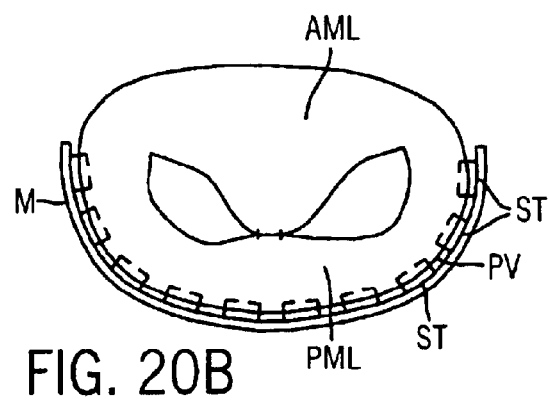
FIG. 20B schematically illustrates a repaired mitral valve during diastole.

FIGS. 20A and 20B show a completed mitral valve repair with two "bow-tie" sutures K placed between the anterior and posterior mitral leaflets AML, PML, and a stapled posterior annuloplasty, inserted in the manner described in connection with FIGS. 19D and 19E. FIG. 20A shows the mitral valve in systole (i.e., closed), and FIG. 20B shows the mitral valve in diastole (i.e., open). The staples ST are connected together by a strip of material M. The strip of material M can be DACRON or polyester, for example. The strip maintains the shape of the posterior valve annulus. Should the posterior valve annulus dilate over time between adjacent staples, the strip of material M prevents expansion of the posterior valve annulus from occurring.

A stapled annuloplasty offers advantages over a conventional annuloplasty. In a conventional annuloplasty, reduction of the mitral valve annulus MVA is accomplished by plicating or folding the valve orifice down to a smaller size so that the valve leaflets come into better contact with one another. This reduction can be done with plicating sutures alone or with plicating sutures that are placed through an annuloplasty ring, which is a ring-shaped device of predetermined size, as will be described in more detail in connection with FIGS. 21–22. As compared to sutures, staples are easier to place, and staples can be placed using less invasive techniques. In addition, in a beating heart, it may be difficult to accurately place and tie multiple sutures. The sutures might become tangled about one another and would be very difficult to untangle. A stapled annuloplasty therefore provides a technique more suitable for use on a beating heart.

Figure 21:
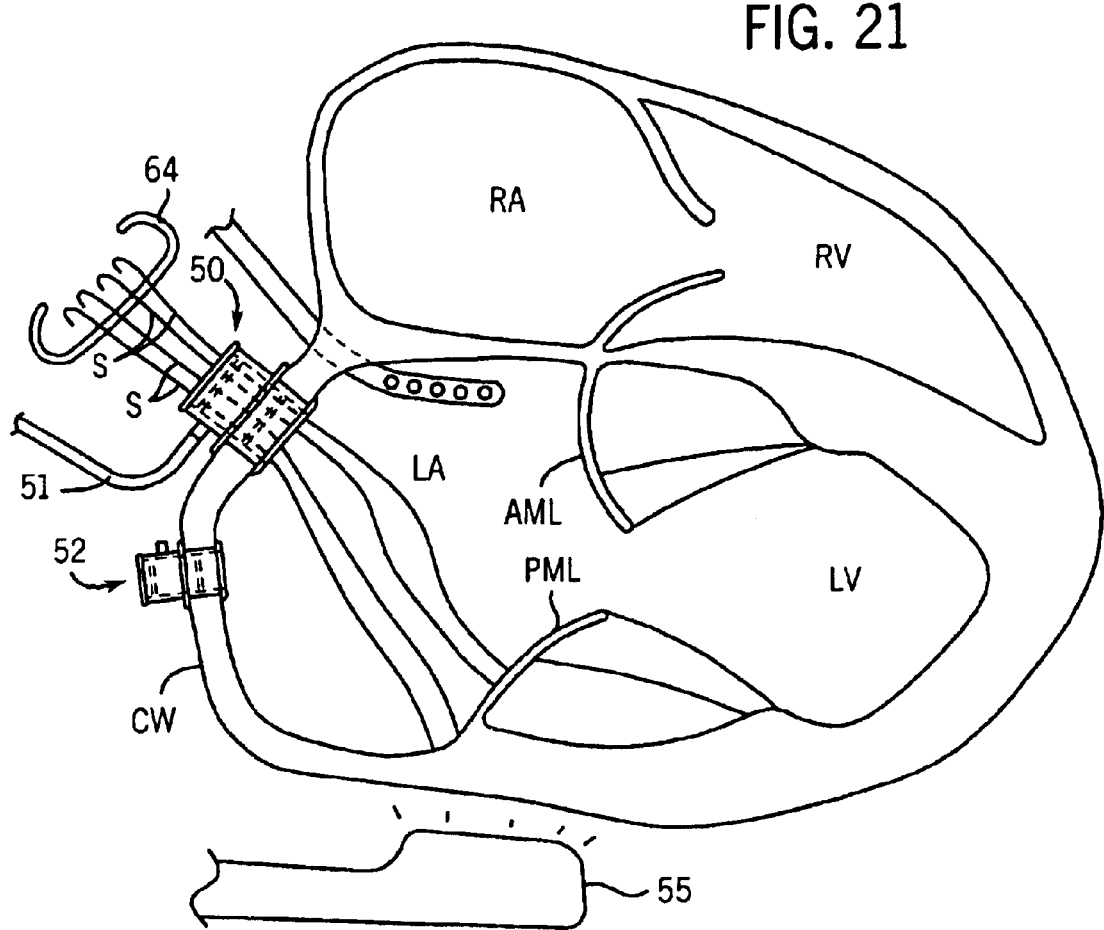
FIG. 21 schematically illustrates sutures extending from the posterior mitral annulus through a cardiac port and an annuloplasty device.
Figure 21A:
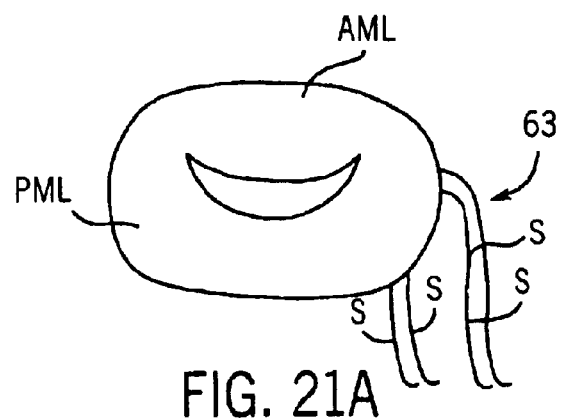
FIG. 21A schematically illustrates a mitral valve having sutures extending through the posterior mitral annulus, as seen in FIG. 21 and as viewed from the left atrium.
Figure 22:
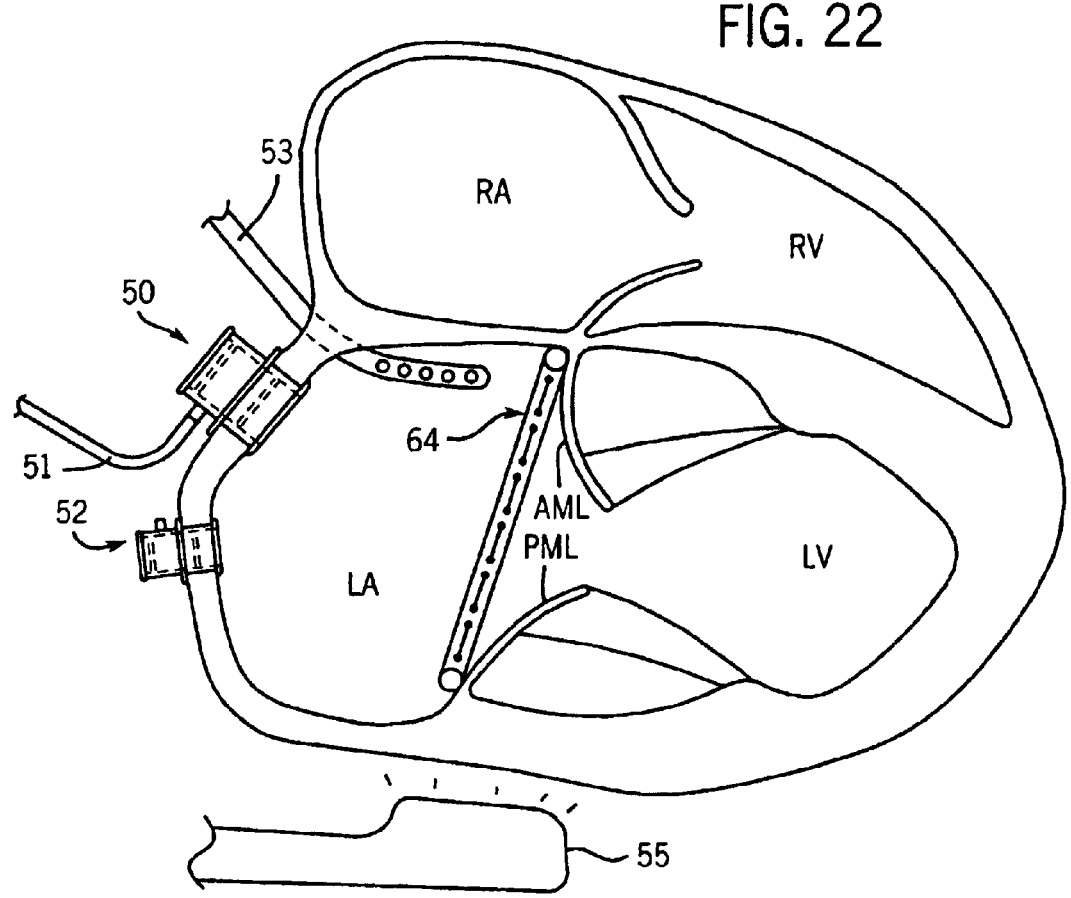
FIG. 22 schematically illustrates an annuloplasty ring implanted in the left atrium to encircle the mitral valve and cover the mitral annulus.

Nevertheless, a conventional annuloplasty ring can be sutured to the mitral valve of a beating heart via a cardiac port in accordance with the invention. FIGS. 21 and 22 illustrate the placement of a conventional flexible annuloplasty device 64, for example, an annuloplasty ring, through a cardiac port 50 of the present invention. The annuloplasty ring 64 is flexible and can be inserted through the cardiac port 50 in a sideways orientation. An endoscopic suture device is used to place multiple interrupted sutures through the posterior mitral annulus, as shown in FIG. 21A. Each of these sutures are brought through the annuloplasty ring 64, as would be done in a conventional open mitral annuloplasty. The ring 64 then is flexed and pushed through the port 50. Once the ring is in place at the mitral valve annulus, the sutures then are tied using an endoscopic knot pusher 59 and cut with the suture cutting device 60 (see FIG. 16). The ring 64 remains seated against the mitral valve annulus as shown in FIGS. 22 and 22A.

Figure 22A:
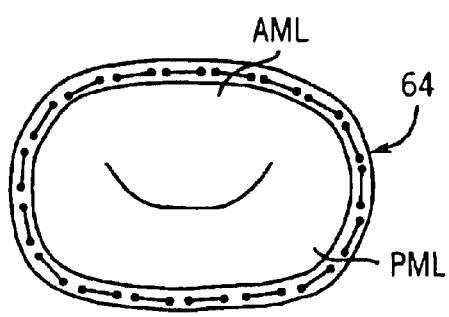
FIG. 22A schematically illustrates a mitral valve encircled by an annuloplasty ring, as seen in FIG. 22 and as viewed from the left atrium.
Figure 22B:
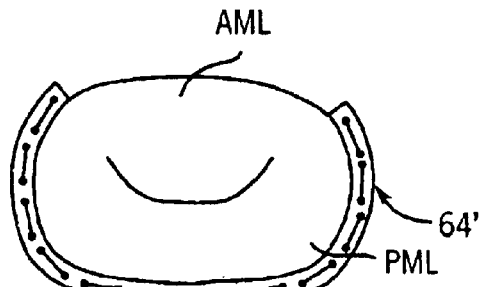
FIG. 22B schematically illustrates a mitral valve partially encircled by an alternative annuloplasty ring, as viewed from the left atrium.

FIGS. 22 and 22A show an annuloplasty ring that completely encircles the mitral valve and covers the entire mitral annulus (i.e., both the anterior mitral annulus and posterior mitral annulus). However, it will be understood that, in this procedure in a beating heart, the annuloplasty ring of FIGS. 22 and 22A can be replaced with an annuloplasty ring that only partially encircles the mitral valve. In particular, it is envisioned that an annuloplasty ring for use in accordance with the invention will include rings 64' that cover only the posterior mitral annulus, i.e., that portion of the valve annulus encircling the posterior mitral leaflet, as, for example, shown in FIG. 22B. The posterior mitral annulus is the portion of the mitral valve that usually dilates. The anterior mitral annulus usually does not dilate because it is attached to the fibrous central core of the heart, which generally remains the same size.

FIG. 16 shows a suture cutting device 60 that can be used in the above-described surgical procedures in accordance with the invention. The suture cutting device 60 has an elongated body 60B and a central lumen 60C. The suture cutting device also includes a wall member 60W extending into the lumen 60C. The wall member 60W separates a knot-receiving chamber 70 and a cutting implement 72. The knot-receiving chamber 70 is defined by a first area on a first side of the wall member 60W, and the cutting implement 72 is disposed in the lumen 60C in a second area on an opposite side of the wall member 60W. The elongated body 60B serves as a protective sheath to isolate the cutting implement from the patient so that the cutting implement cannot cut or cause injury to the heart chamber or other anatomic structures.

The wall member 60W forms a narrowed portion having a hole or channel 60CH therethrough. The channel 60CH matches the caliber of the suture S. A strand of suture S, i.e., a suture arm, can pass up through the channel 60CH and out of the proximal end 60PE of the device 60. In another embodiment, the elongated body 60B can have a suture outlet opening located between the wall member 60W and the proximal end 60PE. The end 58 of the suture can pass through this suture outlet opening so that the suture does not need to be long enough to extend the entire length of the device 60.

The knot-receiving chamber 70 has a greater diameter than the channel 60CH, such that knots K can be accommodated in the knot-receiving chamber 60CH, but cannot pass through the channel 60CH. The knot-receiving chamber can be approximately 7 mm in length, measured from the distal end 60DE of the body 60 to a lower limit of the channel 60H. The channel 60CH has a length of approximately 3–5 mm. Thus, when the cutting edge CE of the cutting implement 72 moves from a first (at rest) position to a second (cutting) position to cut the suture S, the uppermost knot K is 3–5 mm away from the cutting edge CE in the second position (i.e., the knot retains a 3–5 mm tail).

The suture cutting device 60 can be fired, for example, by actuating an actuator, such as push rod 90, connected to the cutting implement 72. Firing the suture cutting device 60 drives the cutting implement 72 from the first position to the second position across the suture S. Because the knot K cannot pass through the channel 60CH, the cutting edge CE of the cutting implement cannot cut the knot K.

The wall member 60W can be annular in shape and can have planar upper and lower surfaces, angled upper and lower surfaces, or a combination thereof. In FIG. 16, the wall member 60W is shown having an upper surface that is planar in one section 76 and angled in another section 78. The cutting implement 72 can be disposed opposite the angled upper surface 78. In this regard, the cutting implement 72 can slide along the angled upper surface 78 of the wall member 60W from a first (at rest) position, shown in FIG. 16, to a second (cutting) position in the direction of arrow B. In addition, the wall member 60W can have a surface 80 that acts as a stop for the cutting implement 72. This stop surface 80 is located opposite the angled upper surface 78. The cutting implement 72 will travel in the direction of arrow B only until cutting edge CE comes into contact with surface 80. The cutting implement 72 then will retract to its first (at rest) position.

The stapling device 62, the suture cutting device 60, and other medical devices used in the above-described minimally invasive diagnostic and surgical procedures can be attached to robotic arms or can be manually manipulated by the surgeon.

As apparent from the above discussion, the present apparatuses and methods for performing minimally invasive diagnostic and surgical procedures inside of a beating heart offer several advantages. For example, due to its unique configuration, the cardiac port of the present invention minimizes air intake into the cardiac chamber, minimizes the risk of emboli, and avoids excessive injury to the cardiac wall. The cardiac port prevents air intake by enabling pressurization of the heart chamber with the patient's own arterial blood. The port extends only a small distance into the intracardiac or intra-chamber area of the heart chamber to avoid inadvertent injury of the chamber wall or valve. Further, the cardiac port may prevent blood loss because it includes at least one valve that prevents blood from leaking out of the cardiac port as instruments are passed through the lumen of the cardiac port.

Preliminary studies of the apparatuses and methods for minimally invasive cardiac surgery have been undertaken. Specifically, the feasibility of performing surgery under echocardiographic guidance was tested in a water bath with silastic sheets simulating the cardiac chambers. The edges of sheet material can be grasped with stapling devices, but, because operating with two-dimensional cross-sectional images provided by TEE is difficult, improvement in the spatial orientation and image resolution is desired to perform important surgical tasks, such as passing a needle from one instrument to another. It was observed that instrument positioning relative to the transducer is also important. All metal instruments create a shadow as they reflect the echo signal, thus obstructing the view of the target areas.

In another preliminary study, post-mortem examinations were performed on two swine sacrificed in a laboratory. It was determined that a left thoracotomy would allow direct access to the mitral valve through the left atrial appendage. Additional small ports could be placed in the dome of the left atrium or at the origin of the left superior pulmonary vein. An animal over 50 kg would be large enough for the required instrumentation.

As a result of the preliminary studies, the following research plan was developed and is in the process of being executed in connection with further studies of the present invention. Purebred Yorkshire female swine (50 to 60 kg) will receive a normal swine food diet and will be housed for a minimum of 1 week. Initial sedation will be achieved with 10 mg/kg IM ketamine. An ear vein then will be cannulated for administration of an infusion of ketamine and thaimylal as needed to supplement anesthesia. The swine will be intubated and ventilated with oxygen at a flow of 2 L/min and isofluorane in a concentration of 1.25%. Isofluorane will be the primary anesthetic agent. Suxamethonium (3 mg IV) will be given as a neuromuscular blocking agent. The femoral vein and both femoral arteries will be cannulated. Continuous pressure monitoring with a pressure transducer advanced to the thoracic aorta will be utilized.

A left thoracotomy will be performed and the left lung deflated by hilar clamping. Heparin (100 mg/kg) will be given. A standard arterial line will be placed in the left femoral artery and connected, through a stopcock, into the left atrium via an 18 gauge IV catheter to increase left atrial pressure, which will minimize the risk of air introduction. Two purse-string sutures will be placed, one in the left atrial wall and one in the left atrial appendage. Cardiac ports in accordance with the invention will be inserted through the purse-strings and secured.

A trans-esophageal echo (TEE) probe, such as the OMINIPLANE device marketed by Hewlett-Packard, will be advanced into position and connected to a monitor, such as the SONOS 1000 marketed Hewlett-Packard. The left atrium will then be imaged (imaging planes chosen as described below). Under TEE guidance, the free edge of the posterior leaflet will be grasped, if needed, with an endoscopic grasper, such as a Genzyme Snowden-Pencer. A single mattress suture will be placed across the posterior leaflet by firing a stitching device, for example, the AUTO-STITCH device marketed by United States Surgical Corporation, or by firing an endoscopic suture placing device, which is an instrument that passes a single or double suture through a structure. The procedure will be repeated for the anterior leaflet. Both sutures will be brought out through the cardiac port. The sutures will be tied together through the port, using an endoscopic knot pusher. This will replicate the Alfiori "bow-tie" mitral valve repair.

Mitral valve function will be examined using TEE. The mitral valve area will be calculated using a standard technique. In brief, under long-axis imaging, transmittal velocities will be measured by an echo Doppler. Using the modified Bernoulli equation, pressure gradients will be calculated. The mitral valve area then can be estimated, using the known pressure half time equation. Video recording will be made. Mitral regurgitation will be estimated by a standard color-flow Doppler technique, and regurgitant jet area and length will be measured.

The swine will be euthanized with 30 cm of KCL. The mitral valve will be inspected for damage and accuracy of suture placement. It is expected that it will take 3–5 animals to develop the basic surgical technique. In animals 1–3, the emphasis will be on imaging and choosing proper port placement sites. Upper-esophageal, mid-esophageal and transgastric TEE positions will be evaluated. Multichamber imaging will be performed in multiple planes at each level. The appropriate imaging planes for surgical manipulation will be identified. Port placement sites on the atrium will be evaluated to choose which sites will allow the appropriate angles of approach to the dynamic valve without shadowing (blocking the echo signal). By animals 3–5, it is expected that appropriate instrumentation to properly constrain the valve leaflets, stapler device firing, and the tying of suture through ports will be identified. These represent new surgical techniques, and a significant learning curve is anticipated. Animals 5–10 will be utilized to demonstrate the reproducibility of the technique.

The beating heart valve surgery of the present invention represents a significant departure from current standard therapy. It has the potential to significantly reduce the morbidity and mortality of mitral valve surgery. Performing mitral valve repair on the beating heart, duplicating mitral valve repair techniques with a suturing device, and the substitution of echocardiography for direct visualization are all novel and unique approaches to cardiac surgery. These surgical techniques provide a stepping block for complex intracardiac repairs performed by small robotic devices placed into the heart using real-time three-dimensional echocardiography to guide the robotic devices.

Given the disclosure of the present invention, one versed in the art will appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

All citations to publications, books, patents, and patent applications set forth herein are incorporated by reference in their entirety.

LIST OF CITATIONS

1. St. Jude Medical Corporation. 1998: Personal Communication.
2. Cohn L H, Ross, M R: Mechanical and bioprosthetic mitral valve replacement, in Edmunds L H J (ed): *Cardiac Surgery in the Adult*, New York, McGraw-Hill, 1997, pp 1025–1050.
3. Cosgrove D M, Sabik J F, Navia J L: Minimally invasive valve operations. *Ann. Thorac. Surg.* 1998;65:1535–1538.
4. Navia J L, Cosgrove D M: Minimally invasive mitral valve operations [see comments]. *Ann. Thorac. Surg.* 1996;62; 1542–1544.
5. Aklog L, Adams D H, Couper G S, Gobezie R, Sears S, Cohn L H: Techniques and results of direct-access minimally invasive mitral valve surgery: a paradigm for the future *J. Thorac. Cardiovasc. Surg.* 1998;116:705–715.
6. Cohn L H, Adams D H, Couper G S, Bichell D P, Rosborough D M, Sears S P, Aranki S F; Minimally invasive cardiac valve surgery improves patient satisfaction while reducing costs of cardiac valve replacement and repair. *Ann. Surg.* 1997;226:421–426.
7. Loulmet D F, Carpentier A, Cho P W, Berrebi A, d'Attellis N, Austin C B, Couetil J P, Lajos P: Less invasive techniques for mitral valve surgery. *J. Thorac. Cardiovasc. Surg.* 1998;115:772–779.
8. Mohr F W, Falk V, Diegeler A, Walther T, van S J, Autschbach R: Minimally invasive port-access mitral valve surgery [see comments]. *J. Thorac. Cardiovasc. Surg.* 1998; 115:567–574.
9. Chitwood W R J. Elbeery J R, Chapman W H, Moran J M, Lust R L, Wooden W A, Deaton D H: Video-assisted minimally invasive mitral valve surgery: the "micromitral" operation [see comments]. *J. Thorac. Cardiovasc. Surg.* 1997; 113:413–414.
10. Gundry S R, Shattuck O H, Razzouk A J, del R M, Sardari F F, Bailey L L: Facile minimally invasive cardiac surgery via ministernotomy. *Ann. Thorac. Surg* 1998;65:1100–1104.
11. Baldwin J C: Editorial (con) re minimally invasive port-access mitral valve surgery [editorial; comment]. *J. Thorac. Cardiovasc. Surg.* 1998;115:563–564.
12. Buckberg G D, Beyersdorf F, Allen B S, Robertson J M: Integrated myocardial management: background and initial application. *J. Card. Surg.* 1995;10:68–89.
13. Kirklin J W: Myocardial management during cardiac surgery with cardiopulmonary bypass, in Kirklin John W, Barratt-Boyes Brian G (eds): *Cardiac Surgery*, New York, Churchill Livingstone, 1993, pp 129–165.
14. Gorman R C, Ziats N, Rao A K. Gikakis N, Sun L, Khan M M, Stenach N, Sapatnekar S, Chouhan V, Gorman J H, Niewiarowski S. Colman R W, Anderson J M, Edmunds L H J: Surface-bound heparin fails to reduce thrombin formation during clinical cardiopulmonary bypass [see comments]. *J. Thorac. Cardiovac. Surg.* 1996; 111:1–11.
15. Edmunds L H J: Blood-surface interactions during cardiopulmonary bypass. *J. Card. Surg* 1993;8:404–410.
16. Chung J H, Gikakis N, Rao A K, Drake T A, Colman R W, Edmunds L H J: Pericardial blood activates the extrinsic coagulation pathway during clinical cardiopulmonary bypass. *Circulation* 1996;93:2014–2018.
17. Edmunds L H J: Why cardiopulmonary bypass makes patients sick: strategies to control the blood-synthetic surface interface. *Adv. Card. Surg.* 1995;6:131–167.
18. Edmunds L H J; Inflammatory response to cardiopulmonary bypass. *Ann. Thorac. Surg.* 1998;66:S12–S16.
19. Downing S W, Edmunds L H J: Release of vasoactive substances during cardiopulmonary bypass [see comments]. *Ann. Thorac. Surg.* 1992;54:1236–1243.
20. Westaby S, Benetti F J: Less invasive coronary surgery: consensus from the Oxford meeting. *Ann. Thorac. Surg.* 1996;62;924–931.
21. Siminelakis S, Bossinakou I, Antoniou F, Pallanza Z, Tolios J, Vasilogiannakopoulou D. Kasapli M, Parigori P, Chlapoutakis E: A study of the effects of extracorporeal circulation on the immunologic system of humans. *J. Cardiothorac. Vasc. Anesth.* 1996;10:893–898.
22. Gill R, Murkin J M: Neuropsychologic dysfunction after cardiac surgery: what is the problem? *J. Cardiothorac. Vasc. Anesth.* 1996;10;91–98.
23. Taylor K M: Brain damage during cardiopulmonary bypass. *Ann. Thorac. Surg.* 1998;65:S20–S26.
24. Taylor K M: Central nervous system effects of cardiopulmonary bypass. *Ann. Thorac. Surg.* 1998;66:S20–S24.
25. Roach G W, Kanchuger M, Mangano C M, Newman M, Nussmeier N, Wolman R, Aggarwal A, Marschall K, Graham S H, Ley C: Adverse cerebral outcomes after coronary bypass surgery. Multicenter Study of Perioperative Ischemia Research Group and the Ischemia Research and Education Foundation Investigators [see comments]. *N. Engl. J. Med.* 1996;335:1857–1863.

26. Jansen E W, Grundeman P F, Borst C, Eefting F, Diephuis J, Nierich A, Lahpor J R, Bredee J J: Less invasive off-pump CABG using a suction device for immobilization: the 'Octopus' method. *Eur. J. Cardiothorac. Surg.* 1997;12:406–412.
27. Takuma S, Homma S: Evaluation of mitral valve disease using transesophageal echocardiography [In Process Citation]. *Semin. Thorac. Cardiovasc. Surg.* 1998;10:247–254.
28. Daniel W G, Mugge A: Transesophageal echocardiography [see comments]. *N. Engl. J. Med.* 1995;332:1268–1279.
29. Foster G P, Isselbacher E M, Rose G A, Torchiana D F, Akins C W, Picard M H: Accurate localization of mitral regurgitant defects using multiplane transesophageal echocardiography. *Ann. Thorac. Surg.* 1998;65: 1025–1031.
30. Takuma S, Zwas D R. Fard A, Wu H, Chaudhry H, Di T M, Ota T, Homma S: Real-time, 3-dimensional echocardiography acquires all standard 2-dimensional images from 2 volume sets: A clinical demonstration in 45 patients [In Process Citation]. *J. Am. Soc. Echocardiogr.* 1999;12:1–6.
31. Umana J P, Salehizadeh B, DeRose J J Jr, Nahar T, Lotvin A, Homma S, Oz M C: "Bow-tie" mitral valve repair: an adjuvant technique for ischemic mitral regurgitation. *Ann. Thorac. Surg.* 1998;66:1640–1646.
32. Morales D L S, Madigan J D, Choudhri A F, Williams M R, Helman D N, Elder J B et al. Development of an off bypass mitral valve repair. *The Heart Surgery Forum* 2000; 2(2):115–120.

What is claimed is:

1. A method of accessing an interior of a heart chamber of a heart, comprising:
    inserting a port into a chamber wall of the heart chamber while the heart remains beating, the port having a lumen therethrough for accessing the interior of the heart chamber from exterior of the heart chamber;
    inserting a stapling device through the lumen of the port; and
    positioning staples from the stapling device into at least a portion of a mitral valve annulus to reduce a length of the portion of the mitral valve annulus.

2. The method of claim 1, wherein the inserting step comprises securing the port in an atrial wall to access an interior of the heart.

3. The method according to claim 1, further comprising the step of connecting the staples together with a strip of material.

4. The method according to claim 1, wherein the positioning step comprises placing staples into the posterior mitral annulus.

* * * * *